(12) United States Patent
Grandt et al.

(10) Patent No.: US 7,794,448 B2
(45) Date of Patent: Sep. 14, 2010

(54) MULTIPLE LUMEN CATHETER AND METHOD OF MAKING SAME

(75) Inventors: Axel Grandt, Strassberg (DE); Randolf Von Oepen, Los Altos Hills, CA (US); Andrew Jeffrey, Tuebingen (DE); Bodo Quint, Rottenburg-Seebronn (DE); Stevan Nielsen, Rottenburg (DE); Thomas Rieth, Hirrlingen (DE)

(73) Assignee: Abbott Laboratories, Abbott, IL (US)

( * ) Notice: Subject to any disclaimer, the term of this patent is extended or adjusted under 35 U.S.C. 154(b) by 1103 days.

(21) Appl. No.: 11/439,596

(22) Filed: May 23, 2006

(65) Prior Publication Data

US 2007/0060910 A1 Mar. 15, 2007

Related U.S. Application Data

(63) Continuation-in-part of application No. 11/136,640, filed on May 23, 2005, now Pat. No. 7,625,353, and a continuation-in-part of application No. 10/952,543, filed on Sep. 29, 2004.

(60) Provisional application No. 60/684,143, filed on May 23, 2005, provisional application No. 60/575,643, filed on May 27, 2004, provisional application No. 60/654,022, filed on Feb. 17, 2005.

(51) Int. Cl.
*A61M 25/00* (2006.01)
(52) U.S. Cl. ..................................................... 604/524
(58) Field of Classification Search ................. 604/264, 604/523, 524, 528, 534, 535
See application file for complete search history.

(56) References Cited

U.S. PATENT DOCUMENTS

| | | |
|---|---|---|
| 4,490,421 A | 12/1984 | Levy |
| 4,563,181 A | 1/1986 | Wijayarathna et al. |
| 4,721,115 A | 1/1988 | Owens |
| 4,748,982 A | 6/1988 | Horzewski et al. |
| 4,762,129 A | 8/1988 | Bonzel |
| 4,771,777 A | 9/1988 | Horzewski et al. |
| 4,877,031 A | 10/1989 | Conway et al. |

(Continued)

FOREIGN PATENT DOCUMENTS

DE 94 20 821 4/1995

(Continued)

OTHER PUBLICATIONS

Restriction Requirement mailed on Mar. 17, 2008 for U.S. Appl. No. 11/136,251.

(Continued)

*Primary Examiner*—Nicholas D Lucchesi
*Assistant Examiner*—Aarti B Berdichevsky
(74) *Attorney, Agent, or Firm*—Baker Botts L.L.P.

(57) ABSTRACT

The invention provides a catheter and method of making the same including an outer tubular member having a length, an outer surface, an inner surface and a lumen therethrough. The catheter also includes an inner tubular member having an outer surface, an inner surface and a lumen therethrough, at least a length of the inner lumen is disposed in the lumen of the outer tubular member. The catheter also includes a support member biasing a portion of the outer surface of the inner tubular member against a portion of the inner surface of the outer tubular member.

27 Claims, 10 Drawing Sheets

U.S. PATENT DOCUMENTS

| | | | |
|---|---|---|---|
| 4,892,519 A * | 1/1990 | Songer et al. ......... 604/102.03 |
| 4,921,483 A | 5/1990 | Wijay et al. |
| 4,944,745 A | 7/1990 | Sogard et al. |
| 5,037,404 A | 8/1991 | Gold et al. |
| 5,047,045 A | 9/1991 | Arney et al. |
| 5,102,403 A | 4/1992 | Alt |
| 5,135,535 A | 8/1992 | Kramer |
| 5,147,317 A | 9/1992 | Shank et al. |
| 5,154,725 A | 10/1992 | Leopold |
| 5,195,978 A | 3/1993 | Schiffer |
| 5,217,482 A | 6/1993 | Keith |
| 5,226,888 A | 7/1993 | Arney |
| 5,252,159 A | 10/1993 | Arney |
| 5,261,879 A | 11/1993 | Brill |
| 5,267,958 A | 12/1993 | Buchbinder et al. |
| 5,300,025 A * | 4/1994 | Wantink ............... 604/103.09 |
| 5,304,198 A | 4/1994 | Samson |
| 5,328,468 A | 7/1994 | Kaneko et al. |
| 5,334,147 A | 8/1994 | Johnson |
| 5,357,978 A | 10/1994 | Turk |
| 5,370,615 A | 12/1994 | Johnson |
| 5,395,334 A | 3/1995 | Keith et al. |
| 5,410,797 A | 5/1995 | Steinke et al. |
| 5,413,557 A | 5/1995 | Solar |
| 5,413,560 A | 5/1995 | Solar |
| 5,425,711 A | 6/1995 | Ressemann et al. |
| 5,443,457 A | 8/1995 | Ginn et al. |
| 5,460,185 A | 10/1995 | Johnson et al. |
| 5,470,315 A | 11/1995 | Adams |
| 5,480,383 A | 1/1996 | Bagaoisan et al. |
| 5,489,271 A | 2/1996 | Anderson |
| 5,490,837 A | 2/1996 | Blaeser et al. |
| 5,496,346 A | 3/1996 | Horzewski et al. |
| 5,500,180 A | 3/1996 | Anderson et al. |
| 5,538,510 A | 7/1996 | Fontirroche et al. |
| 5,545,138 A | 8/1996 | Fugoso et al. |
| 5,549,553 A | 8/1996 | Ressemann et al. |
| 5,549,563 A | 8/1996 | Kronner et al. |
| 5,588,964 A | 12/1996 | Imran et al. |
| 5,605,543 A | 2/1997 | Swanson |
| 5,634,902 A | 6/1997 | Johnson et al. |
| 5,649,909 A | 7/1997 | Cornelius |
| 5,656,029 A | 8/1997 | Imran et al. |
| 5,658,251 A | 8/1997 | Ressemann et al. |
| 5,662,622 A | 9/1997 | Gore et al. |
| 5,667,493 A | 9/1997 | Janacek |
| 5,669,932 A | 9/1997 | Fischell et al. |
| 5,695,483 A | 12/1997 | Samson |
| 5,702,439 A | 12/1997 | Keith et al. |
| 5,711,909 A | 1/1998 | Gore et al. |
| 5,728,067 A | 3/1998 | Enger |
| 5,733,400 A | 3/1998 | Gore et al. |
| 5,738,667 A | 4/1998 | Solar |
| 5,743,875 A * | 4/1998 | Sirhan et al. ............. 604/96.01 |
| 5,755,685 A | 5/1998 | Anderson |
| 5,755,687 A * | 5/1998 | Donlon .................... 604/508 |
| 5,775,685 A | 7/1998 | Yamaoka et al. |
| 5,807,355 A | 9/1998 | Ramzipoor et al. |
| 5,820,594 A | 10/1998 | Fontirroche et al. |
| 5,820,613 A | 10/1998 | Van Werven-Franssen et al. |
| 5,823,995 A | 10/1998 | Fitzmaurice et al. |
| 5,824,173 A | 10/1998 | Fontirroche et al. |
| 5,833,604 A | 11/1998 | Houser et al. |
| 5,836,965 A | 11/1998 | Jendersee et al. |
| 5,843,032 A | 12/1998 | Kastenhofer |
| 5,843,050 A | 12/1998 | Jones et al. |
| 5,851,464 A | 12/1998 | Davila et al. |
| 5,882,336 A | 3/1999 | Janacek et al. |
| 5,891,056 A | 4/1999 | Ramzipoor |
| 5,891,110 A | 4/1999 | Larson et al. |
| 5,902,290 A | 5/1999 | Peacock, III et al. |
| 5,938,645 A * | 8/1999 | Gordon ...................... 604/264 |
| 5,951,539 A | 9/1999 | Nita et al. |
| 5,980,486 A | 11/1999 | Enger |
| 6,004,291 A | 12/1999 | Ressemann et al. |
| 6,010,521 A | 1/2000 | Lee et al. |
| 6,017,323 A | 1/2000 | Chee |
| 6,027,477 A | 2/2000 | Kastenhofer |
| 6,030,405 A | 2/2000 | Zarbatany et al. |
| 6,036,670 A | 3/2000 | Wijeratne et al. |
| 6,036,715 A | 3/2000 | Yock |
| 6,059,770 A | 5/2000 | Peacock, III et al. |
| 6,066,114 A | 5/2000 | Goodin et al. |
| 6,071,273 A | 6/2000 | Euteneuer et al. |
| 6,102,890 A | 8/2000 | Stivland et al. |
| 6,123,698 A | 9/2000 | Spears et al. |
| 6,129,708 A | 10/2000 | Enger |
| 6,152,909 A * | 11/2000 | Bagaoisan et al. .......... 604/523 |
| 6,159,229 A | 12/2000 | Jendersee et al. |
| 6,165,166 A | 12/2000 | Samuelson et al. |
| 6,187,130 B1 | 2/2001 | Berard et al. |
| 6,193,686 B1 | 2/2001 | Estrada et al. |
| 6,210,364 B1 | 4/2001 | Anderson et al. |
| 6,254,549 B1 | 7/2001 | Ramzipoor |
| 6,273,874 B1 | 8/2001 | Parris |
| 6,273,899 B1 | 8/2001 | Kramer |
| 6,283,939 B1 | 9/2001 | Anderson et al. |
| 6,306,105 B1 | 10/2001 | Rooney et al. |
| 6,306,124 B1 | 10/2001 | Jones et al. |
| 6,309,402 B1 | 10/2001 | Jendersee et al. |
| 6,319,244 B2 | 11/2001 | Suresh et al. |
| 6,344,029 B1 | 2/2002 | Estrada et al. |
| 6,361,529 B1 | 3/2002 | Goodin et al. |
| 6,368,302 B1 | 4/2002 | Fitzmaurice et al. |
| 6,402,720 B1 | 6/2002 | Miller et al. |
| 6,475,184 B1 | 11/2002 | Bruce et al. |
| 6,475,209 B1 | 11/2002 | Larson et al. |
| 6,488,694 B1 | 12/2002 | Lau et al. |
| 6,527,789 B1 | 3/2003 | Lau et al. |
| 6,530,938 B1 | 3/2003 | Lee et al. |
| 6,565,588 B1 | 5/2003 | Clement et al. |
| 6,575,958 B1 | 6/2003 | Happ et al. |
| 6,575,993 B1 | 6/2003 | Yock |
| 6,579,278 B1 | 6/2003 | Bencini |
| 6,633,648 B1 | 10/2003 | Bauck |
| 6,648,854 B1 | 11/2003 | Patterson et al. |
| 6,652,507 B2 | 11/2003 | Pepin |
| 6,663,648 B1 | 12/2003 | Trotta |
| 6,685,720 B1 | 2/2004 | Wu et al. |
| 6,685,721 B1 | 2/2004 | Kramer |
| 6,692,460 B1 | 2/2004 | Jayaraman |
| 6,695,812 B2 | 2/2004 | Estrada et al. |
| 6,702,750 B2 | 3/2004 | Yock |
| 6,702,781 B1 | 3/2004 | Reifart et al. |
| 6,733,473 B1 | 5/2004 | Reifart et al. |
| 6,733,487 B2 | 5/2004 | Keith et al. |
| 6,770,038 B2 | 8/2004 | Balbierz et al. |
| 6,814,744 B2 | 11/2004 | Yang et al. |
| 6,818,001 B2 | 11/2004 | Wulfman et al. |
| 6,821,281 B2 | 11/2004 | Sherman et al. |
| 6,821,287 B1 | 11/2004 | Jang |
| 6,887,219 B2 | 5/2005 | Wantink |
| 6,893,417 B2 | 5/2005 | Gribbons et al. |
| 6,979,342 B2 | 12/2005 | Lee et al. |
| 7,001,358 B2 | 2/2006 | Fitzmaurice et al. |
| 7,025,258 B2 | 4/2006 | Chang |
| 7,037,291 B2 | 5/2006 | Lee et al. |
| 7,118,551 B1 | 10/2006 | Lee et al. |
| 7,309,334 B2 | 12/2007 | Von Hoffmann |
| 2001/0021840 A1 | 9/2001 | Suresh et al. |
| 2001/0034514 A1 | 10/2001 | Parker |
| 2002/0007146 A1 | 1/2002 | Omaleki et al. |
| 2003/0105427 A1 | 6/2003 | Lee et al. |
| 2003/0163082 A1* | 8/2003 | Mertens ...................... 604/43 |

| | | | |
|---|---|---|---|
| 2004/0010243 | A1 | 1/2004 | Klint |
| 2004/0019322 | A1 | 1/2004 | Hoffmann |
| 2004/0193140 | A1 | 9/2004 | Griffin et al. |
| 2004/0236367 | A1 | 11/2004 | Brown et al. |
| 2005/0059292 | A1 | 3/2005 | Hayashi et al. |
| 2005/0131387 | A1 | 6/2005 | Pursley |
| 2006/0270977 | A1 | 11/2006 | Fisher et al. |
| 2007/0078439 | A1* | 4/2007 | Grandt et al. ............... 604/523 |
| 2007/0167913 | A1 | 7/2007 | Elkins et al. |

FOREIGN PATENT DOCUMENTS

| | | |
|---|---|---|
| DE | 97 29 499 | 1/1999 |
| EP | 0 029 185 | 5/1981 |
| EP | 0 408 198 | 1/1991 |
| EP | 0 414 350 | 2/1991 |
| EP | 0 518 205 | 12/1992 |
| EP | 0 806 220 | 11/1997 |
| EP | 0 916 359 | 5/1999 |
| EP | 1435252 | 7/2004 |
| EP | 1 518 581 | 3/2005 |
| WO | WO 92/17236 | 10/1992 |
| WO | WO 98/56448 | 12/1998 |
| WO | WO 01/70321 | 9/2001 |
| WO | WO 2005/113047 | 12/2005 |
| WO | WO 2005/118044 | 12/2005 |
| WO | WO 2005/118045 | 12/2005 |
| WO | WO 2006/104591 | 10/2006 |

OTHER PUBLICATIONS

Response to the Restriction Requirement filed on Apr. 14, 2008 for U.S. Appl. No. 11/136,251.
Non-Final Rejection mailed on Jun. 2, 2008 for U.S. Appl. No. 11/136,251.
Response to the non-Final Rejection mailed on Jun. 2, 2008 filed on Sep. 2, 2008 for U.S. Appl. No. 11/136,251.
Examiner Interview Summary Record mailed on Dec. 17, 2008 for U.S. Appl. No. 11/136,251.
Interview Summary and Supplemental Amendment filed on Dec. 19, 2008 for U.S. Appl. No. 11/136,251.
Notice of Allowance mailed on Jan. 13, 2009 for U.S. Appl. No. 11/136,251.
Issue Fee Payment received on Mar. 20, 2009 for U.S. Appl. No. 11/136,251.
Restriction Requirement mailed on Mar. 13, 2008 for U.S. Appl. No. 11/136,640.
Response to the Restriction Requirement filed on Apr. 14, 2008 for U.S. Appl. No. 11/136,640.
Non-Final Rejection mailed on Jun. 2, 2008 for U.S. Appl. No. 11/136,640.
Response to the non-Final Rejection mailed on Jun. 2, 2008 filed on Sep. 2, 2008 for U.S. Appl. No. 11/136,640.
Examiner Interview Summary Record mailed on Dec. 16, 2008 for U.S. Appl. No. 11/136,640.
Interview Summary and Supplemental Amendment filed on Dec. 19, 2008 for U.S. Appl. No. 11/136,640.
Notice of Allowance mailed on Jan. 12, 2009 for U.S. Appl. No. 11/136,640.
Request for Continued Examination (RCE) filed on Mar. 20, 2009 for U.S. Appl. No. 11/136,640.
Notice of Allowance mailed on Jun. 8, 2009 for U.S. Appl. No. 11/136,640.
Non-Final Rejection mailed on Nov. 3, 2008 for U.S. Appl. No. 11/357,775.
Response to the non-Final Rejection mailed on Nov. 3, 2008 filed on Feb. 3, 2009 for U.S. Appl. No. 11/357,775.
Final Rejection mailed on May 18, 2009 for U.S. Appl. No. 11/357,775.
Request for Continued Examination (RCE) and Amendment after Final Rejection filed on Aug. 17, 2009 for U.S. Appl. No. 11/357,775.
Preliminary Amendment filed on Aug. 18, 2006 for U.S. Appl. No. 11/439,809.
Restriction Requirement mailed on Jul. 29, 2008 for U.S. Appl. No. 11/439,809.
Response to the Restriction Requirement filed on Aug. 25, 2008 for U.S. Appl. No. 11/439,809.
Non-Final Rejection mailed on Sep. 3, 2008 for U.S. Appl. No. 11/439,809.
Notice of Abandonment mailed on May 1, 2009 for U.S. Appl. No. 11/439,809.
Non-Final Rejection mailed on Nov. 14, 2008 for U.S. Appl. No. 11/439,591.
Response to the non-Final Rejection mailed on Nov. 14, 2008 filed on Feb. 17, 2009 for U.S. Appl. No. 11/439,591.
Notice of Non-Compliant Amendment mailed on Mar. 25, 2009 for U.S. Appl. No. 11/439,591.
Response to the non-Final Rejection mailed on Nov. 14, 2008 filed on Apr. 16, 2009 for U.S. Appl. No. 11/439,591.
Final Rejection mailed on Jul. 24, 2009 for U.S. Appl. No. 11/439,591.
Non-Final Rejection mailed on Nov. 4, 2008 for U.S. Appl. No. 11/439,592.
Response to the non-Final Rejection mailed on Nov. 4, 2008 filed on Feb. 4, 2009 for U.S. Appl. No. 11/439,592.
Final Rejection mailed on May 19, 2009 for U.S. Appl. No. 11/439,592.
Request for Continued Examination (RCE) and Amendment after Final Rejection filed on Aug. 17, 2009 for U.S. Appl. No. 11/439,592.

* cited by examiner

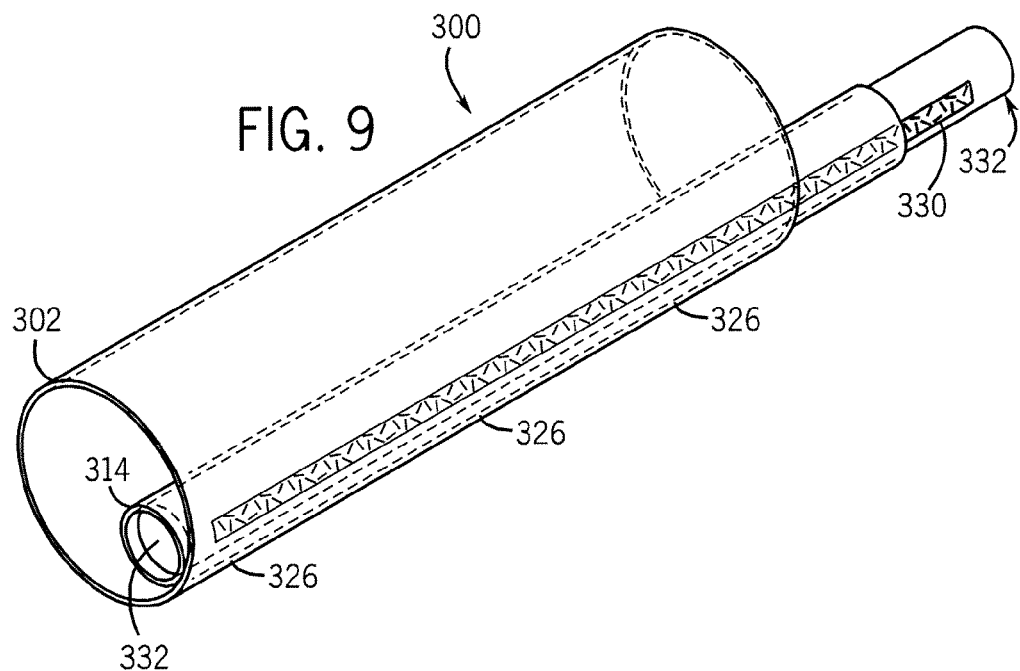
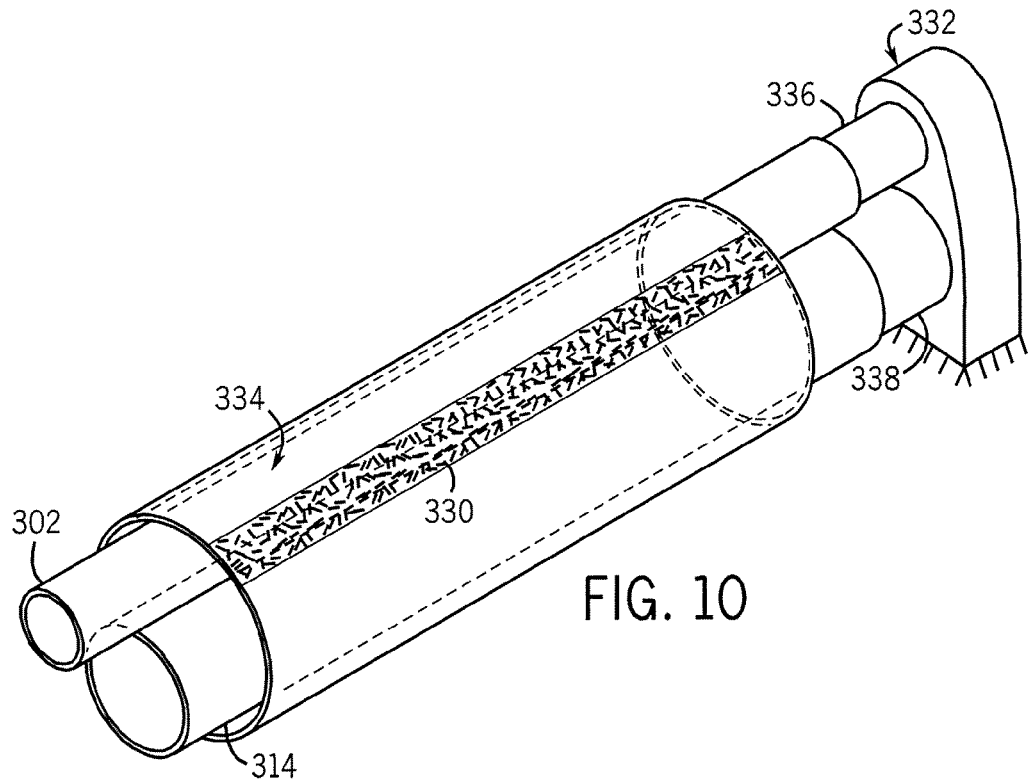

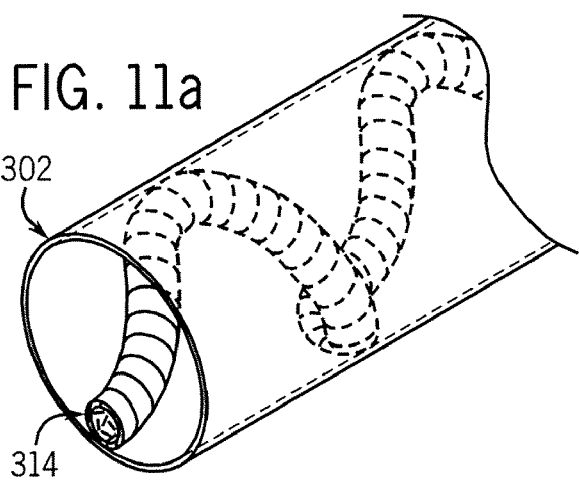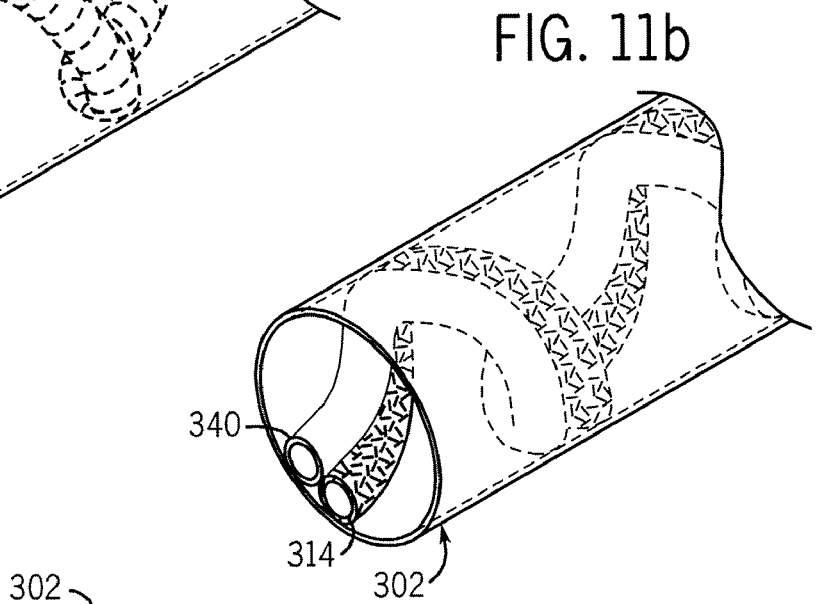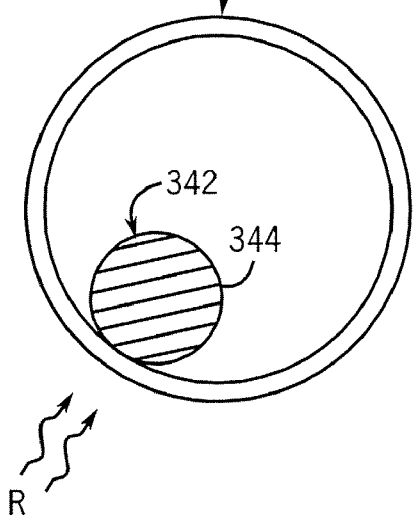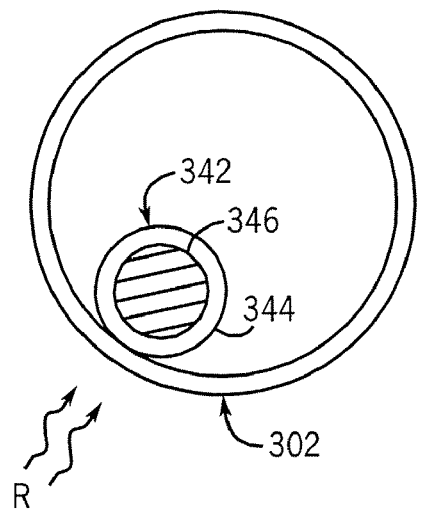

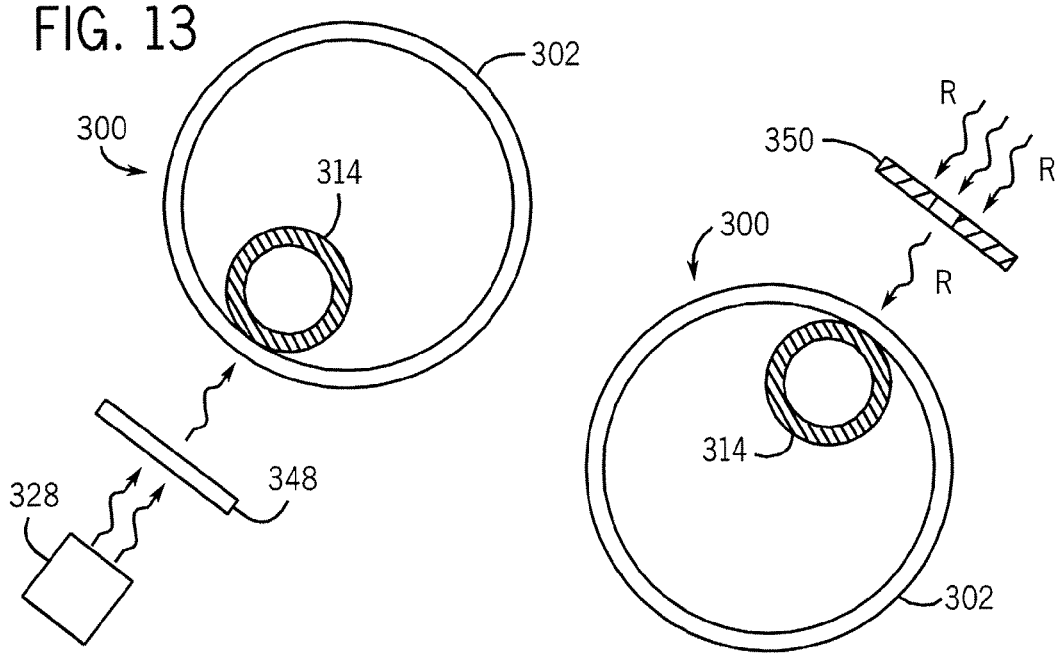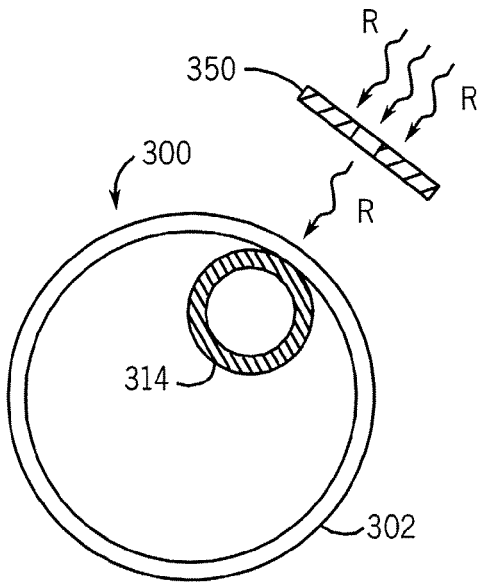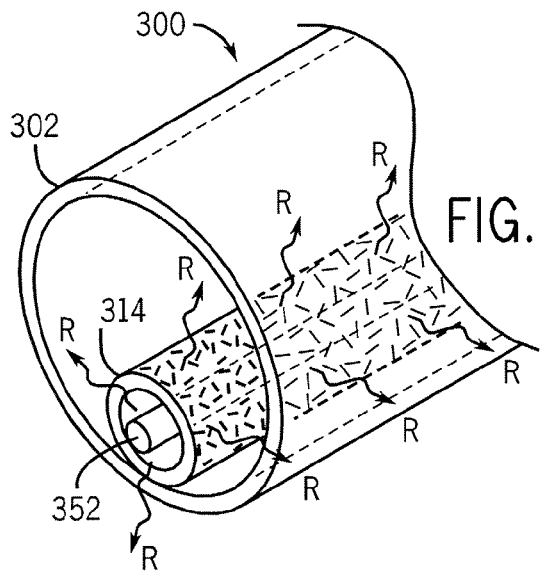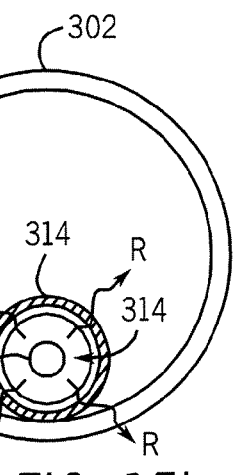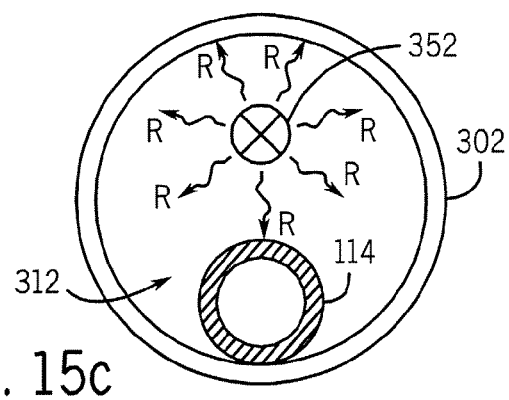

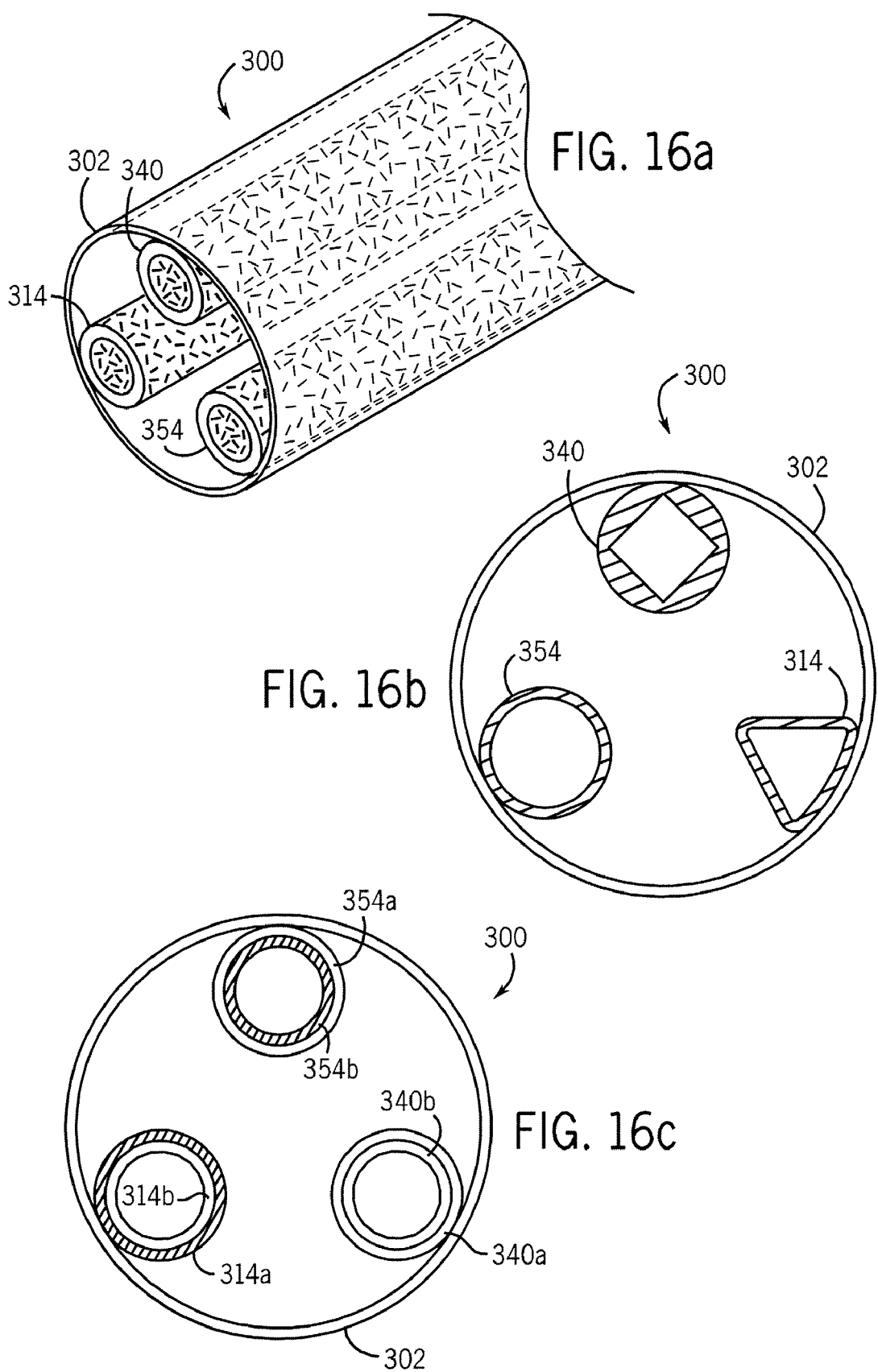

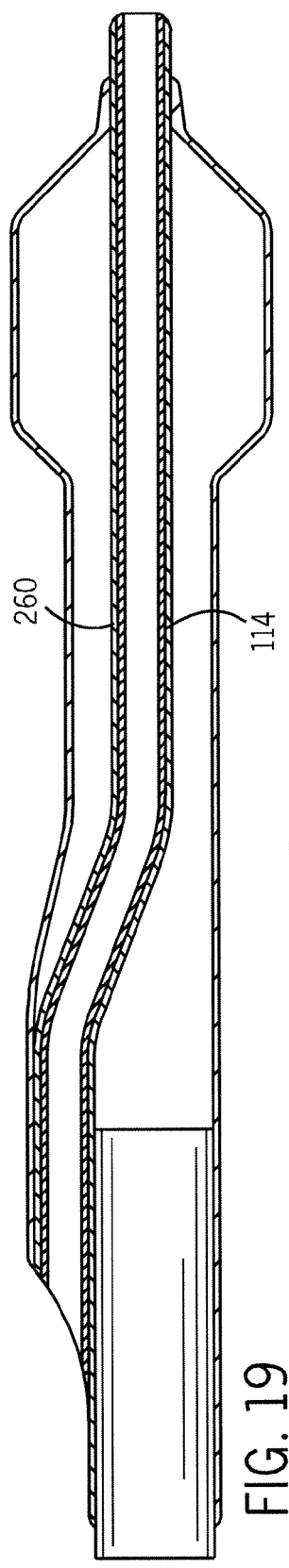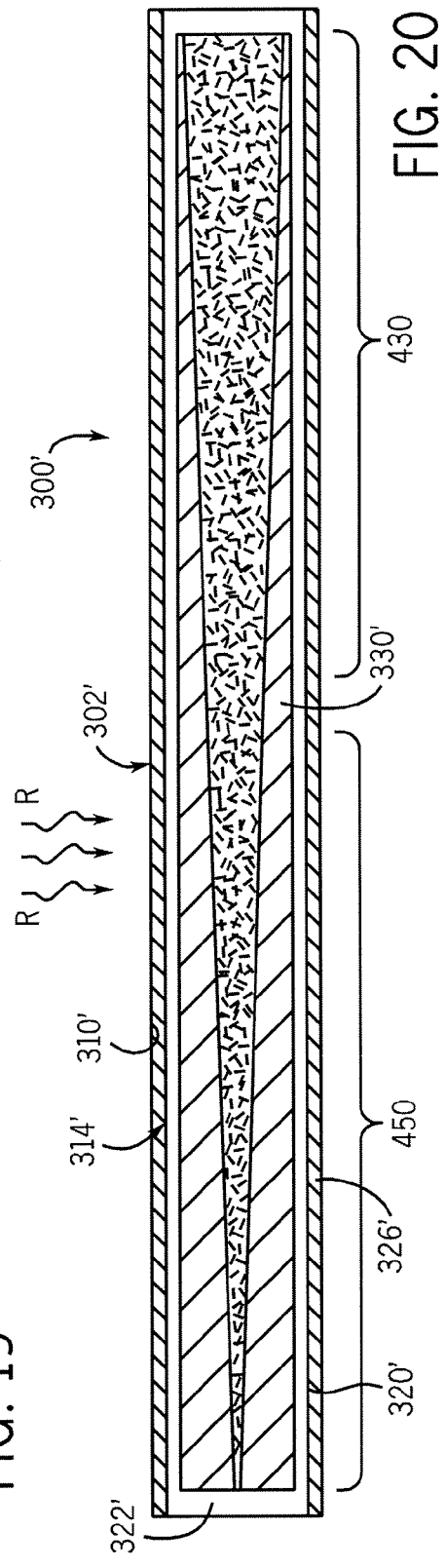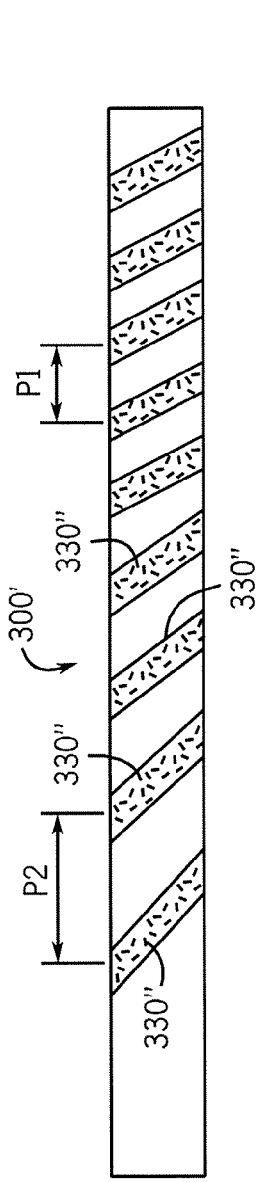

MULTIPLE LUMEN CATHETER AND METHOD OF MAKING SAME

CROSS REFERENCE TO RELATED APPLICATION

The present application claims the benefit of U.S. Provisional Patent Application Ser. No. 60/684,143, filed May 23, 2005 and is a continuation-in-part of U.S. patent application Ser. No. 11/136,640, filed May 23, 2005 now U.S. Pat. No. 7,625,353, and which claims the benefit of U.S. Provisional Patent Application Ser. Nos. 60/575,643 filed on May 27, 2004, and 60/654,022 filed on Feb. 17, 2005, and a continuation-in-part of U.S. patent application Ser. No. 10/952,543, filed Sep. 29, 2004 currently pending, the entire contents of each are incorporated herein by reference.

BACKGROUND OF THE INVENTION

1. Field of the Invention

The present invention relates to a catheter for treating a lumenal system of a patient. Particularly, the present invention is directed to a catheter having a support member disposed in the lumen of an outer tubular member proximate an inner tubular member, where the support member biases a portion of an outer surface of the inner tubular member against a portion of an inner surface of the outer tubular member.

2. Description of Related Art

A variety of catheter devices are known in the art for treating the lumenal system of a patient. Of such devices, many are directed to treating the cardiovascular system of a patient.

"Over the wire" catheters are generally known in the art. These devices are generally introduced into a patient after a guidewire has been introduced into the patient, and advanced to a treatment site within a patient where a treatment procedure (e.g., angioplasty and/or stent placement) is to be performed. The catheter is advanced over the guidewire to the treatment site, the treatment procedure is performed, and the catheter and guidewire are subsequently removed. Such systems can be disadvantageous. Because the guidewire lumen of an over the wire catheter must traverse the entire length of the catheter (which can exceed about 150 cm), either an extremely long guidewire (greater than 300 cm in length) or a guidewire extension must be used to permit the physician to maintain a grip on the guidewire and catheter during the treatment procedure.

To address this problem, rapid exchange catheters have been developed. Generally, a rapid exchange catheter has a relatively short guidewire lumen (e.g., less than 25 cm) near the distal end of the catheter, thus permitting the physician to use a standard length guidewire (e.g., 150-175 cm) to introduce a catheter and/or perform a catheter exchange.

Such conventional methods and systems generally have been considered satisfactory for their intended purpose. However, rapid exchange catheters still suffer from certain performance issues, such as a lack of pushability and kink resistance. Although solutions to this problem have been developed, such as by introducing metallic components (such as hypotubes) along the length of a catheter not supported by a guidewire, there still remains a continued need in the art for a catheter having enhanced pushability, kink resistance and versatility. There also remains a need in the art for a catheter that is inexpensive and easy to make. The present invention provides a solution for these problems.

SUMMARY OF THE INVENTION

The purpose and advantages of the present invention will be set forth in and apparent from the description that follows, as well as will be learned by practice of the invention. Additional advantages of the invention will be realized and attained by the methods and systems particularly pointed out in the written description and claims hereof, as well as from the appended drawings.

To achieve these and other advantages and in accordance with the purpose of the invention, as embodied herein and broadly described, the invention includes a catheter including an outer tubular member having a length, an outer surface, an inner surface and a lumen therein. The catheter also includes an inner tubular member having an outer surface, an inner surface and a lumen therein, at least a length of the inner lumen is disposed in the lumen of the outer tubular member. The catheter also includes a support member disposed in the lumen of the outer tubular member adjacent the inner tubular member, the support member biasing a portion of the outer surface of the inner tubular member against a portion of the inner surface of the outer tubular member.

In accordance with a further aspect of the invention, the support member can be unattached to at least one of the inner tubular member and the outer tubular member. Furthermore, the support member can be unattached to either the inner tubular member or the outer tubular member. The support member can be a tubular structure having a length and a lumen therein. The tubular structure can be at least partially compressed to bias the inner tubular member against the outer tubular member. The support member can be made of a polymeric material, such as polyimide, or an elastomeric member or foam.

In accordance with another aspect of the invention, the support member can extend longitudinally along at least a portion of the length of the inner tubular member disposed within the outer tubular member. The support member can extend along the entire length of the inner tubular member disposed within the outer tubular member. Moreover, a plurality of support members can be disposed along the length between the outer surface of the inner tubular member and the inner surface of the outer tubular member. Furthermore, the plurality of support members can be interconnected. In accordance with a further aspect of the invention, each support member can have a length and the lengths of the support members can be varied.

In accordance with another aspect of the invention, the lumen of the inner tubular member can define a guidewire lumen. The lumen of the outer tubular member can define an inflation lumen. The support member can have a lumen defined therein for passage of inflation fluid. The catheter can further include an inflatable member in fluid communication with the inflation lumen.

In accordance with still another aspect of the invention, a catheter is provided including an elongate main body including at least a proximal shaft section, a distal shaft section, and a lumen therein. The catheter also can include a guidewire tube disposed along a length of the lumen of the elongate main body, and having a proximal guidewire port, a distal guidewire port, and a guidewire lumen therebetween. The catheter can also be provided with a support member disposed in the lumen of the elongate main body adjacent the guidewire tube, the support member biasing a portion of an outer surface of the guidewire tube against a portion of an inner surface of the elongate main body.

In accordance with yet a further aspect of the invention, the support member can be a tubular structure having a length and a lumen therein. The tubular structure can be at least partially compressed to bias the guidewire tube against the elongate main body. Moreover, the support member can extend longitudinally along at least a portion of the length of the guidewire tube disposed within the elongate main body. In accordance with this aspect of the invention, the lumen of the elongate main body can define an inflation lumen. Furthermore, the support member can have a lumen defined therein for passage of inflation fluid.

In further accordance with the invention, the catheter includes at least one tubular member including a plurality of cuts spirally disposed about the outer surface of the tubular member. In this manner, the support member, the guidewire tubular member or the elongate main body can include a plurality of cuts along a length thereof. In this aspect of the invention, the plurality of cuts can transition from a first pitch to a second pitch. The first pitch and second pitch being different. In this manner, the tubular member can be configured to have a varied flexibility along a length thereof. If desired, the tubular member further include coating on at least a portion of the outer surface. For example, a polymeric coating, e.g., polyamide, polyimide, or a block copolymer such as Pebax® can form a topcoat on the surface of the tubular member.

The invention also includes a catheter tubing and method for forming a catheter tubing. In one embodiment, the catheter tubing defines a multiple lumen catheter. Alternatively, the catheter tubing can define a multi-layered unitary catheter tube.

The method for forming a catheter tubing includes providing a first tubular member having a proximal end, a distal end, and a first lumen therein and a second tubular member having a proximal end, a distal end, and a second lumen therein. The method includes the further step of arranging the first tubular member in contact with the second tubular member to define a contact area therebetween. The method also includes providing a light absorbing portion proximate to the contact area, and irradiating the light absorbing portion with light energy to fuse the second tubular member to the first tubular member at the fixation or contact area. The light absorbing portion is configured to include a gradient along its length. A fusion bond is defined by the absorption of light energy by the light absorbing portion. The fusion bond includes a gradient that corresponds to the gradient of the light absorbing portion. Accordingly, in one aspect of the invention, the method is capable of defining catheter tubing having a varied stiffness or flexibility along its length.

In further accordance with the invention, the providing step can include positioning at least one mandrel having a light absorbing portion proximate to the contact area, and irradiating the mandrel with light energy to fuse the second tubular member to the first tubular member at the contact area. Moreover, the irradiating step can include irradiating the mandrel with white light. The white light can be provided by a halogen light source. The light absorbing portion can include a linear segment along a length of the mandrel. The providing step can include locating the mandrel in the lumen of at least one of the first and second tubular members with the light absorbing portion proximate the contact area. The contact area can be defined along at least a portion of the length of the first and second tubular members. The arranging step can include disposing at least a length of the second tubular member inside the lumen of the first tubular member with a portion of the outer surface of the second tubular member in contact with a portion of the inner surface of the first tubular member to define the contact area therebetween. Furthermore, the first lumen can define an inflation lumen, and the second lumen can define a guidewire lumen.

In accordance with a further aspect of the invention, the providing step can include locating the mandrel in the lumen of the second tubular member with the light absorbing portion proximate the contact area. The light absorbing portion can include a linear segment. In accordance with yet a further aspect of the invention, the light absorbing portion can include a plurality of segments.

In accordance with another aspect of the invention, the providing step can include locating the mandrel outside the outer surface of the first tubular member with the light absorbing portion proximate the contact area. The arranging step can also include disposing at least a length of the first tubular member proximate a length of the second tubular member with the outer surface of the first tubular member in contact with the outer surface of the second tubular members.

In accordance with still another aspect of the invention, the method can further include the step of applying a pre-fixation device to at least one of the first and second tubular members to temporarily hold the first and second tubular members together prior to the irradiating step. The pre-fixation device can include removable heat shrink tubing. The arranging step can include disposing at least a length of the second tubular member inside the lumen of the first tubular member. Furthermore, the pre-fixation device can include a removable insert disposed in the lumen of the first tubular member having a cross dimension sufficient to bias a portion of the outer surface of the second tubular member against a portion of the inner surface of the first tubular member.

In accordance with another aspect of the invention, at least one of the first or second tubular members can be transparent and/or non-absorbing to light energy. Moreover, the mandrel can further define a pre-fixation device. The pre-fixation device can include shrink wrap tubing, the shrink wrap tubing having a colored area to define a light absorbing portion.

It is to be understood that both the foregoing general description and the following detailed description are exemplary and are intended to provide further explanation of the invention claimed.

The accompanying drawings, which are incorporated in and constitute part of this specification, are included to illustrate and provide a further understanding of the method and system of the invention. Together with the description, the drawings serve to explain the principles of the invention.

BRIEF DESCRIPTION OF THE DRAWINGS

FIG. 9 is an isometric view of a portion of a representative embodiment of a catheter made in accordance with a variation of the method of the present invention.

FIG. 10 is a partial isometric view of still another alternative embodiment of a catheter made in accordance with a method of the present invention.

FIGS. 11(a)-11(b) are partial isometric views of a portion of an alternative embodiment of a catheter made in accordance with the present invention.

FIGS. 12(a)-12(b) are end views of a cross section of a catheter made in accordance with an alternative embodiment of the present invention.

FIG. 13 is an end view of a cross section of a catheter made in accordance with the method of the present invention.

FIG. 14 is a depiction of an alternative embodiment of a method of fabricating a catheter in accordance with the present invention.

FIGS. 15(a)-15(c) are a depiction of still another alternative embodiment of a method of fabricating a catheter in accordance with the present invention.

FIGS. 16(a)-16(c) are perspective and end views of portions of alternative catheters made in accordance with the present invention.

FIG. 19 is an illustration of a catheter including a tubular member having a plurality of cuts along its length in accordance with the present invention.

FIG. 20 is an illustration of a method of fusing first and second tubular members in accordance with the present invention; and FIG. 21 is a depiction of one embodiment of a light absorbing portion having a gradient along its length in accordance with the invention.

DETAILED DESCRIPTION OF THE PREFERRED EMBODIMENT

Reference will now be made in detail to the present preferred embodiments of the invention, an example of which is illustrated in the accompanying drawings. The method and corresponding steps of the invention will be described in conjunction with the detailed description of the system.

The devices and methods presented herein may be used for treating the lumenal systems of a patient. The present invention is particularly suited for treatment of the cardiovascular system of a patient, such as performance of angioplasty and delivery of balloon-expandable or self-expanding interventional devices (e.g., stents, filters, coils).

In accordance with the invention, a catheter is provided including an outer tubular member having a length, an outer surface, an inner surface and a lumen therein. The catheter also includes an inner tubular member having an outer surface, an inner surface and a lumen therein, at least a length of the inner lumen is disposed in the lumen of the outer tubular member. In a preferred embodiment, the inner tubular member is secured against the inner surface of the outer tubular member. In accordance with one aspect of the invention, the catheter also includes a support member disposed in the lumen of the outer tubular member adjacent the inner tubular member, the support member biasing a portion of the outer surface of the inner tubular member against a portion of the inner surface of the outer tubular member.

Figure 1:
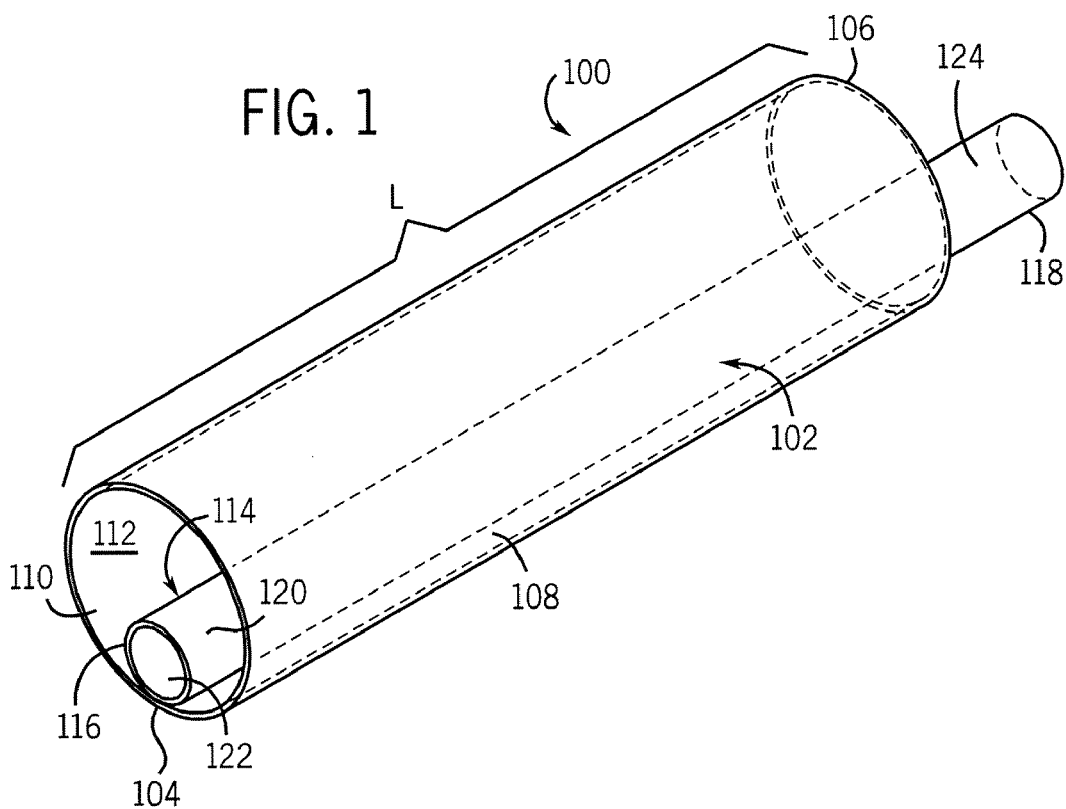
FIG. 1 is an isometric view of a portion of a first representative embodiment of a catheter in accordance with the present invention.

For purpose of explanation and illustration, and not limitation, a partial view of an exemplary embodiment of the catheter in accordance with the invention is shown in FIG. 1 and is designated generally by reference character 100. Other embodiments of a catheter in accordance with the invention, or aspects thereof, are provided in FIGS. 2-21, as will be described.

In accordance with the invention, an outer tubular member is provided having a length, an outer surface, an inner surface and a lumen therein.

For purposes of illustration and not limitation, as embodied herein and as depicted in FIG. 1, catheter 100 is provided with an outer tubular member 102. Outer tubular member 102 has a proximal end 104, a distal end 106, a length L, an outer surface 108, an inner surface 110 and defines a lumen 112 therein.

Outer tubular member 102 can be made from a variety of materials, including metal, plastic and composite materials. Metal tubes such as stainless steel hypotubes can be used, and may or may not be coated with a polymeric material such as PTFE. Multilayered polymeric tubes can also be used formed by coextrusion, dipping processes, or by shrinking tubing layers over one another over a mandrel. Moreover, polymeric tubular members can also be formed by charging a mandrel with static electricity, applying plastic in powder or granular form to the mandrel to form a layer of plastic over the mandrel, and by heating the mandrel to cause the particles to fuse. Multilayered polymeric tubes can also be used that include metallic or nonmetallic braiding within or between layers of the tube. A carbon tube can also be used, as well as fiber-reinforced resin materials. If the catheter is only comprised of a single outer tubular along its length, it may be desirable in certain instances to design outer tubular member 102 to have a decreasing stiffness along its length from proximal end 104 to distal end 106.

In further accordance with the invention, a catheter is provided further including an inner tubular member.

For purposes of illustration and not limitation, as embodied herein and as depicted in FIG. 1, catheter 100 includes inner tubular member 114. Inner tubular member 114 has a proximal end 116, a distal end 118, an outer surface 120, an inner surface 122 and defines a lumen 124 therein. In accordance with a particular embodiment of the invention depicted in FIG. 1, at least a length of the inner tubular member 114 is disposed in the lumen of the outer tubular member 102.

Figure 2:
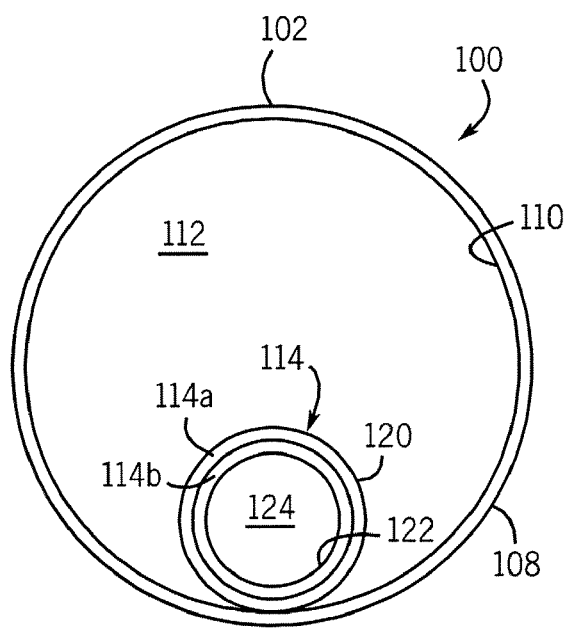
FIG. 2 is an end view of the portion of the catheter of FIG. 1 in accordance with the present invention.

A variety of materials can be used for inner tubular member 114. For example and not limitation, as depicted in FIG. 2, inner tubular member 114 can be made from the same materials as the outer tubular member 102. In accordance with a specific embodiment of the invention, a multilayered tube is used for inner tubular member 114 including a nylon outer layer 114a and an inner layer 114b formed from a lubricious material such as polyethylene of varying densities, PTFE, polyimide, PEEK or PVDF. In accordance this aspect of the invention, the inner tubular member 114 can function as a guidewire lumen, as the low friction inner surface 122 of inner tubular member permits a guidewire to move easily through lumen 124.

In accordance with another specific embodiment of the invention, as depicted in FIG. 19, inner tubular member 114 can be formed from a metallic tube. For example and not limitation, the metallic tube can be formed from stainless steel, nitinol, or any other suitable metal or metal alloy. In further accordance with this embodiment, the metallic tube can further include a plurality of cuts or markings 260 along a length thereof to define an inner tubular member having an increased flexibility or stiffness along its length. The metallic tube can include a plurality of cuts 260 over a portion of the inner tubular member or if desired along the entire length thereof. Additionally or alternatively, the elongate main body can be configured to define a tubular member having a plurality of cuts along a length thereof, if desired.

In one preferred embodiment, the plurality of cuts 260 is disposed in a helical or spiral pattern along the length of the inner tubular member 114. The helical pattern defines a plurality of rotations about the tubular member. A pitch P is defined between adjacent rotations. The inner tubular member 114 can be configured to include a plurality of cuts 260 along its length having a constant pitch along a portion of the inner tubular member. Alternatively, the tubular member 114 can be configured to include a plurality of cuts 260 having a progressive pitch, i.e., an increasing or decreasing, along a portion of the inner tubular member. As yet another example, the pitch can be varied along a length thereof. For example and not limitation, a first portion of the tubular member can include a plurality of cuts 260 having a constant pitch, and a second portion of the tubular member can include a plurality of cuts having a varied pitch.

In this regard, the first portion can have include cuts having a pitch from about 0.5 to 2 mm, and a second portion can have a plurality of cuts having a pitch that ranges from 1 to 2 mm, 3 to 4 mm, 4 to 5 mm. Alternatively, a first portion of the tubular member can have a plurality of cuts 260 having a constant pitch and a second portion of the tubular member 114 can have a plurality of cuts 260 having a decreasing pitch. Generally, the pitch can have a length from about 0.1 to about 100 mm. A pitch from about 0.5 to 20 mm is preferred. However, other suitable pitch lengths are suitable depending on the stiffness or flexibility desired. The inner tube can be configured to have an increasing flexibility or stiffness along a length thereof by varying the pitch along the sections of the tubular member.

In further accordance of the invention, the metallic tube can further include a coating, preferably a polymeric coating 262, over a length thereof. A variety of polymeric materials can be used. For example and not limitation, the polymers can include polyamide, polyimide, block copolymers, including PTFE and Pebax®, and the like. Alternatively, other suitable coating materials can be used as would be known in the art.

For example and not limitation, the metallic tubular member can be formed by laser cutting a hypotube in a desired pattern over a portion or the entire length of the hypotube. However, other suitable techniques can be used to form the cuts 260 along the tubular member 114, as would be known in the art. Further, a polymeric coating 262 can be extruded over a length of the inner body if desired.

In further accordance with the invention, the catheter includes a support member configured to bias a portion of the outer surface of the inner tubular member against a portion of the inner surface of the outer tubular member.

Figure 3:
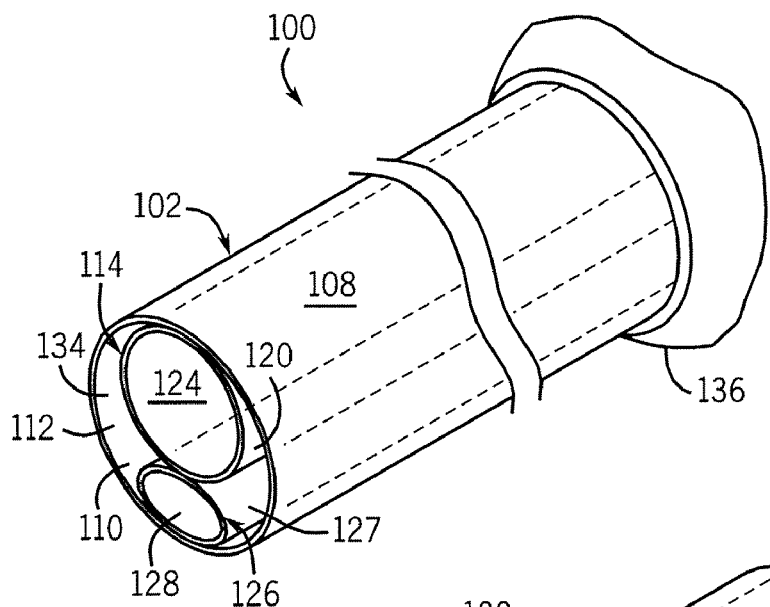
FIG. 3 is an isometric view of a portion of a second representative embodiment of a catheter in accordance with the present invention.

For purposes of illustration, and not limitation, as depicted in FIG. 3, catheter 100 includes support member 126. As depicted, support member 126 is disposed in the lumen 112 of the outer tubular member 102 adjacent the inner tubular member 114. The support member 126 is configured to bias a portion of the outer surface 120 of the inner tubular member 114 against a portion of the inner surface 110 of the outer tubular member 102. Such an arrangement is advantageous as it enhances the structural integrity of catheter 100.

Support member can take on a variety of forms. For purposes of illustration only, as depicted in FIG. 3, support member 126 can include a tubular structure having a length and defining a lumen 128 therein. This tubular structure can be at least partially compressed to bias the inner tubular member 114 against the outer tubular member 102. In accordance with this aspect of the invention, the support member 126 can be made, for example, of a metallic material, a polymeric material, such as polyimide, or an elastomeric member or foam. However, other materials such as shape memory materials can also be used. If a shape memory material is used, support member 126 can be configured to expand from a first undeployed configuration to a second deployed configuration upon interaction of support member 126 to a stimulus, such as heat, electricity, chemicals or the like. If desired, the support member can be a metallic tubular member having a plurality of cuts along a length thereof as described herein.

Figure 4:
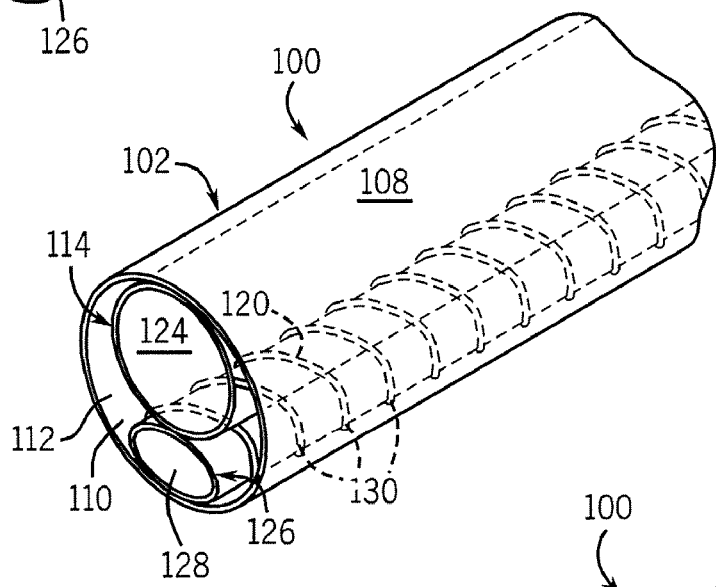
FIG. 4 is an isometric view of a portion of a third representative embodiment of a catheter in accordance with the present invention.

By way of further example, for purposes of illustration only, as depicted in FIG. 4, the support member 126 can have a coiled configuration. The windings 130 of the support member 126 can urge the inner tubular member 114 against the outer tubular member 102. Support member 126 can be made from a variety of materials, including various metals, plastics, fiber-reinforced resins, carbon and combinations thereof. During catheter construction, use of a coiled support member 126 can be advantageous since the overall diameter of the coiled member can be minimized during insertion of support member 126 inside of outer tubular member 102. The diameter of support member 126 can then be increased by unwinding it after insertion to urge inner tubular member 114 against outer tubular member 102. By way of further example, a coiled member of shape-memory material can be used for support member 126 that expands from a first contracted configuration to a larger configuration upon interaction of the coiled support member 126 to a stimulus, such as by a change in temperature (i.e., cooling or heating). In accordance with a specific embodiment of the invention, the coiled member is made from Nitinol. Moreover, the support member can also be a stent-like structure such like a wallstent-structure In further accordance with the invention, the length of the support member can be varied with respect to the other portions of the catheter.

For purposes of illustration and not limitation, as depicted in FIG. 4, support member 126 extends longitudinally along a portion of the length of the inner tubular member 114 disposed within the outer tubular member 102. Alternatively, as depicted in FIG. 3, the support member 126 extends along the entire length of the inner tubular member 102 disposed within the outer tubular member 102.

Figure 5:
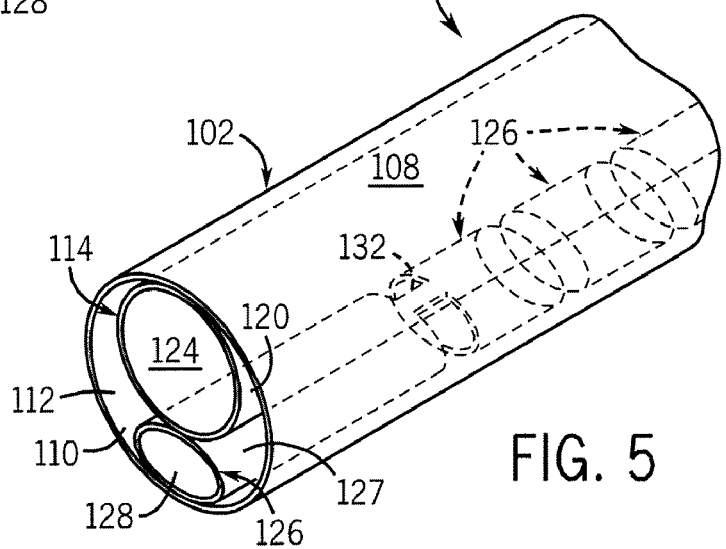
FIG. 5 is an isometric view of a portion of a fourth representative embodiment of a catheter in accordance with the present invention.

By way of further example, as depicted in FIG. 5, a plurality of support members 126 are disposed along the length between the outer surface 120 of the inner tubular member 114 and the inner surface 110 of the outer tubular member 102. Additionally, the plurality of support members 126 can be interconnected by bridge portions 132, if desired.

As additionally depicted in FIG. 5, for purposes of illustration and not limitation, each support member 126 can be provided with a predetermined length whereby the lengths of the support members 126 are varied. The lengths of the support members 126 can be varied to provide a desired change in stiffness along the length of the catheter 100. For example, if it is desired to provide decreasing stiffness along the length of catheter 100, support members 126 can be provided having progressively shorter lengths in the distal direction of the catheter 100.

In further accordance with the invention, the support member can be attached or unattached to various portions of the catheter.

For purposes of illustration only, support member 126 can be unattached to at least one of the inner tubular member 114 and the outer tubular member 102. Alternatively, support member 126 can be unattached to both the inner tubular member 114 and the outer tubular member 102. Such an arrangement can permit for easier assembly of catheter 100. The outer surfaces 120, 127 of one or more of the inner tubular member 114 and support member 126 and the inner surface 110 of the outer tubular member 102 can be provided with a textured surface that causes the parts of the catheter 100 to effectively lock together and not move after the catheter 100 is assembled. Additionally or alternatively, if the surfaces are not configured to lock, this can allow for movement between the members when the catheter is bent.

In further accordance with the invention, the outer tubular member can define an inflation lumen to direct inflation fluid to inflate an inflatable member.

For purposes of illustration and not limitation, as depicted in FIG. 3, outer tubular member 102 defines an inflation lumen 134 generally between inner surface 110 of outer tubular member 102 and outer surface 120 of inner tubular member 114. In accordance with this embodiment of the invention, inflation lumen 134 can be used to direct inflation fluid to an inflatable member 136 in fluid communication with the inflation lumen 134. In accordance with this embodiment of the invention, support member 126 is configured to permit passage of inflation fluid. As such, the support member 126 can help to define the inflation lumen 134.

Inflatable member 136 can be made from a variety of materials. For purpose of illustration and not limitation, inflatable member 136 can be made from a poly ether block amide ("PEBA"), nylon, Hytrel, PU, PEEK, PE or a variety of other materials. Inflatable member 136 can be attached to distal end 106 of outer tubular member 102 of catheter 100 by way of adhesive bond, fusion bond, or preferably by welding, as described in U.S. patent application Ser. No. 10/952,543, which is incorporated by reference herein in its entirety. Thus, if inflatable member 136 is made of nylon, it is advantageous for outer tubular member 102 to be made of a material compatible for a welded bond therebetween.

By way of further example, an inflation device (not shown) is provided for inflating the inflatable member 136. The inflation device 136 can be, for example, a syringe or a flexible reservoir that is connected to a proximal end 104 of outer tubular member 102 and actuated by the physician to inflate inflatable member 136.

In further accordance with the invention, a catheter is provided having an elongate main body including at least a proximal shaft section, a distal shaft section and a lumen therein. Optionally, the catheter can include a guidewire tube.

Figure 6:
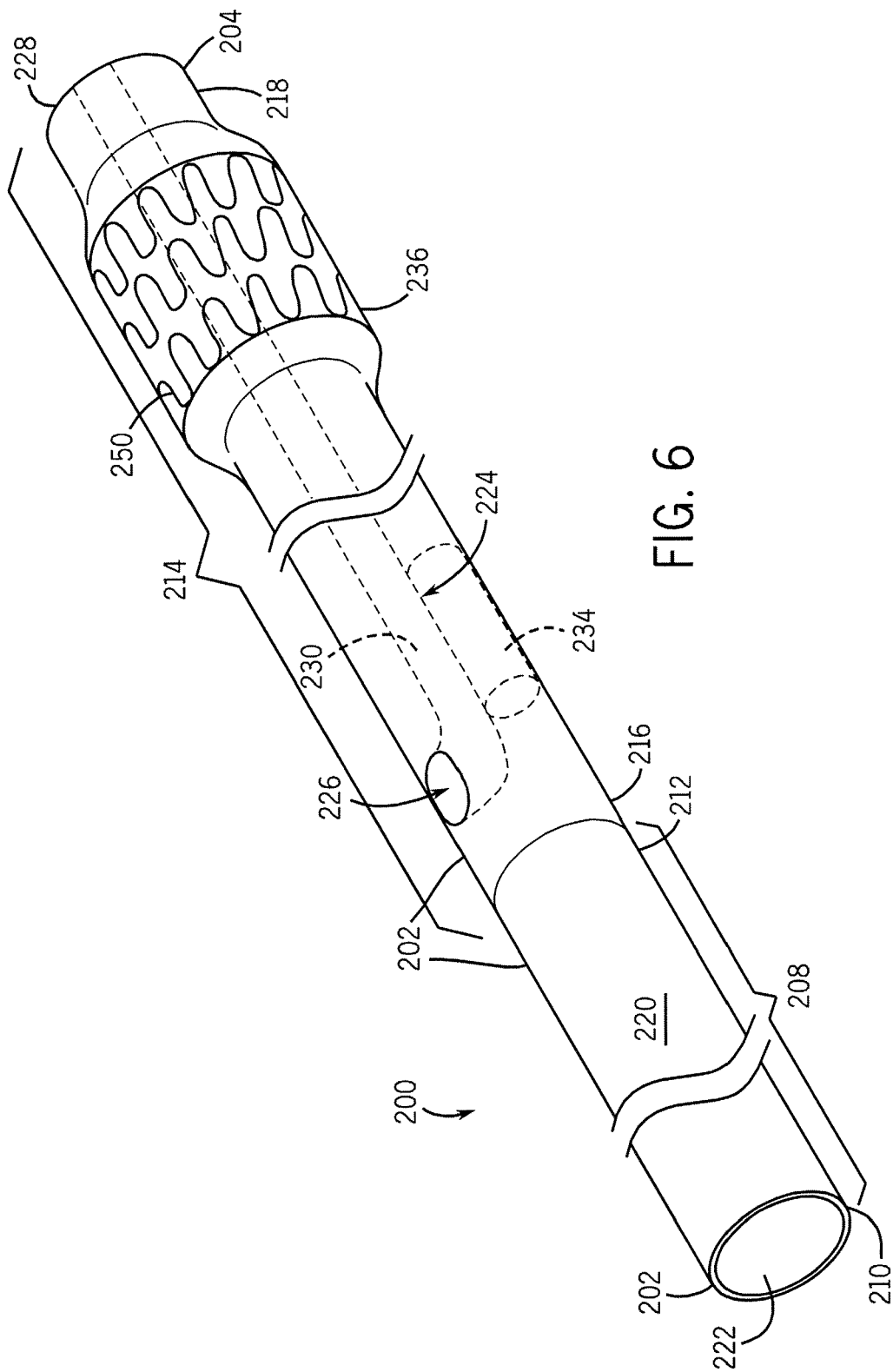
FIG. 6 is an isometric view of a portion of a fifth representative embodiment of a catheter in accordance with the present invention.

For further purposes of illustration and not limitation, as depicted in FIG. 6, a catheter 200 is provided including an elongate main body 202 including a proximal end 202 and a distal end 204. Catheter 200 further includes a proximal shaft section 208 having a proximal end 210 and a distal end 212, as well as a distal shaft section 214 including a proximal end 216, a distal end 218, and a lumen 220 therein having an inner surface 222.

Catheter 200 also can include a guidewire tube 224 disposed along a length of the lumen 220 of the elongate main body 202. Guidewire tube 224 alone or in combination with elongate main body 202 can thus define a proximal guidewire port 226, a distal guidewire port 228, and a guidewire lumen 230 therebetween. The catheter 200 can also be provided with a support member 234 disposed in the lumen 220 of the elongate main body 202 adjacent the guidewire tube 224, the support member 234 biasing a portion of an outer surface 232 of the guidewire tube 224 against a portion of an inner surface 222 of the elongate main body 202. The support member 234 can be formed in a variety of ways as described herein.

Proximal shaft section 208 can be formed of a variety of different materials. Proximal shaft section 208 can be formed from a variety of materials, including metal, plastic and composite materials. Metal tubes such as stainless steel hypotubes can be used, and may or may not be coated with a polymeric material such as PTFE. Multilayered polymeric tubes can also be used formed by coextrusion, dipping processes, or by shrinking tubing layers over one another over a mandrel or by electrostatic deposition and heating as described herein above. Multilayered polymeric tubes can also be used that include metallic or nonmetallic braiding within or between layers of the tube. A carbon tube can also be used, as well as fiber-reinforced resin materials. It may be desirable in certain instances to design proximal shaft section 208 to have a decreasing stiffness along its length from proximal end 210 to distal end 212.

Constructing proximal shaft section 208 from a relatively stiff material can provide catheter 200 with enhanced pushability and kink resistance during use, particularly if catheter 200 is designed for use as a rapid-exchange catheter such that proximal shaft section 208 is not supported along its length by a guidewire during use. Moreover, a hypotube can act as a fluid conduit, or inflation lumen, if catheter 200 is provided with a inflatable member 236, as depicted in FIG. 6.

A variety of materials can also be used for distal shaft section 214. For example, distal shaft section 214 can be made from any suitable polymer material such as Polyamide, PEEK, PTFE, PVDF, Kynar, or polyethylene of various suitable densities. As a further exemplary alternative, distal shaft section 214 can be a composite member comprising a fabrication of several different materials, such as a co-extrusion of different polymers, or a fiber-reinforced composite material such as fiber-reinforced resin or polymeric thermoplastic material. While it is generally desired that distal shaft section 214 be more flexible than proximal shaft section 208, distal shaft section 214 can also be as stiff or even stiffer than proximal shaft section 208, depending on the desired application of catheter 200.

In accordance with another aspect of the invention, the catheter of the present invention can be used to deliver a medical device to a location within the corporeal system of a patient.

For purposes of illustration and not limitation, as embodied herein, a variety of medical devices are suitable for delivery by the catheter of the present invention. For purpose of example and not limitation, a medical device can be provided, for example, in the form of a balloon-expandable stent 250 as depicted in FIG. 6. Such devices are generally well known in the art. However, the catheter of the present invention is not limited to the delivery of balloon expandable stents. Other devices may also be used. For example, stent-grafts, self-expanding intraluminal devices, coils, filters and embolic protection devices may be delivered within a patient's vasculature using the catheter of the present invention. Other devices such as a prosthesis retrieval mechanism or visual or ultrasonic imaging devices can also be delivered with the catheter to a predetermined location in a patient's lumenal systems. Moreover, combinations of medical devices and/or beneficial agents can also be delivered using the device of the present invention. For example, multiple stents or a combination of stents and embolic protection devices and/or beneficial agents can be delivered using the catheter of the present invention, mounted on separate inflatable members (not shown) or as self expanding devices or coils and combinations of coils and stent-grafts or the like.

Figure 7:
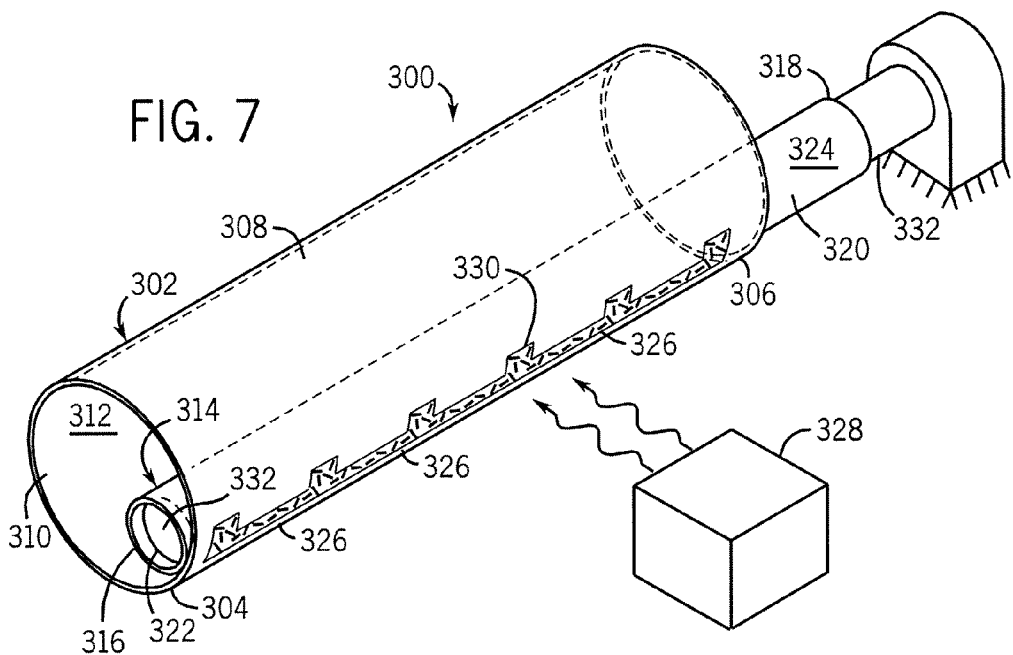
FIG. 7 is an isometric view of a portion of a representative embodiment of a catheter made in accordance with the method of the present invention.

In accordance with another aspect of the invention, as shown and embodied in FIGS. 7 and 20, a catheter tubing 300, 300' and a method of forming a catheter tubing are provided. The catheter tubing includes a first tubular member 302, 302' having a proximal end, a distal end, a lumen therein, a second tubular member 314, 314' having a proximal end, a distal end, a lumen therein, and a fusion area disposed between the first tubular member and the second tubular member. The fusion area has an intensity gradient. The intensity gradient defines a varied stiffness along a length of the fusion area.

In one embodiment, the lumen of the first tubular member 302, 302' is larger than the lumen of the second tubular member. In this manner, the second tubular member 314, 314' can be disposed inside the lumen of the first tubular member 302, 302'. Further, each lumen can be configured such that the first and second tubular members define a multiple lumen catheter tubing, as shown in FIG. 7. In this embodiment, the contact area 326 between the first and second tubular members is disposed along a portion of the inner surface of the outer tubular member and the outer surface of the inner tubular member. Accordingly, and as depicted in FIG. 7, the lumen 312 of the first tubular member can define an inflation lumen and the lumen 324 of the second tubular member can define a guidewire lumen.

In another embodiment, each of the first and second tubular lumens can be configured to define a multi-layer tubing, as shown and embodied in FIG. 20. In this embodiment, as shown in FIG. 20, the contact area 326' between the first and second tubular members is disposed along a portion of the inner surface 310' of the first tubular member and the outer surface of the second tubular member 320'. Accordingly, a unitary lumen 322' is provided to define a guidewire lumen or alternatively an inflation lumen, if desired.

In one preferred embodiment, at least one of the tubular members is sufficiently transparent to light energy. For example, in one embodiment, the first tubular member is formed from a material that is sufficiently transparent to light energy and the second tubular member includes a light absorbing portion. The light absorbing portion of the second tubular member absorbs irradiated light energy sufficient to form a fusion area between the first and second tubular members.

In one embodiment, as depicted in FIGS. 7 and 20, the light absorbing portion 330, 330' includes an intensity gradient along a length thereof. For example and not limitation, as shown in FIG. 20, the intensity gradient includes a dark colored area having an increasing or decreasing density along the length of the light absorbing portion.

Further, and in accordance with the invention, the fusion area between the first and second tubular members has an intensity gradient which corresponds to the intensity gradient of the light absorbing portion 330, 330'. In this manner, the intensity gradient defines a variation in stiffness or flexibility along the length of the multilayer or multilumen tubing defined by the tubular members.

In a further aspect of the invention, a method of forming the multilayer tubing 300' or the multilumen tubing 300 is provided. The method includes the step of providing a first tubular member having a proximal end, a distal end, and a first lumen therein and a second tubular member having a proximal end, a distal end, and a second lumen therein.

For purposes of illustration and not limitation, as embodied herein and as depicted in FIG. 7, a first tubular member 302 and a second tubular member 314 are provided for forming a catheter 300. First tubular member 302 includes a proximal end 304, a distal end 306, an outer surface 308 an inner surface 310 and a lumen 312. Second tubular member 314 includes a proximal end 316, a distal end 318, an outer surface 320, an inner surface 322 and a lumen 324. These tubular members 302, 314 can be similar in composition and construction to outer tubular member 102 and inner tubular member 114 described herein. One or both of first tubular member 302 and second tubular member 314 can be composed of material sufficiently transparent to permit passage of light therethrough.

In further accordance with the invention, the method includes the further step of arranging the first tubular member in contact with the second tubular member to define a contact area therebetween.

For purposes of illustration and not limitation, as embodied herein and as depicted in FIG. 7, the arranging step can include disposing at least a length of the second tubular member 314 inside the lumen 312 of the first tubular member 302 with a portion of the outer surface 320 of the second tubular member 314 in contact with a portion of the inner surface 322 of the first tubular member 302 to define a contact area 326 therebetween.

In accordance with one embodiment of the invention, as depicted in FIG. 7, lumen 312 of first tubular member 302 can define an inflation lumen, and lumen 324 of second tubular member 314 can define a guidewire lumen. One of the lumens can also be used for injection of cells (for gene therapy), and therapeutic or beneficial agents, such as anticoagulants and the like. Alternatively, and in accordance with another embodiment of the invention, as depicted in FIG. 20, the first tubular member 302' can define an outer layer and the second tubular member 314' can define an inner layer of a multilayer tubing 300'.

In further accordance with the invention, as depicted in FIGS. 7 and 20, the method includes positioning a light absorbing portion 330, 430 proximate to the contact area 326, 326' and irradiating the first and second tubular members and the light absorbing portion 330, 330' with light energy to fuse the second tubular member to the first tubular member at the contact area.

In a preferred embodiment, light absorbing portion 330, 330' has an intensity gradient along a length thereof. The intensity gradient, as shown in FIGS. 20 and 21, includes a dark color having an increasing or decreasing density along a length thereof. For the purpose of illustration and not limitation, the light absorbing portion having an intensity gradient can be a linear segment, which has a decreasing width along the length of the light absorbing portion. The decreasing width can be varied, as depicted in FIG. 7, or progressive, as depicted in FIG. 20. Alternatively, the predetermined shape can comprise a plurality of interrupted segments 330" along the length of the light absorbing portion, as shown in FIG. 21. The plurality of interrupted segments can be configured to define alternating dark and light areas along the length of the light absorbing portion. For example, the plurality of interrupted segments can include helical shaped dark areas. In this manner, as depicted in FIG. 21, a pitch (P1, P2) can be defined between adjacent helices and the length of the pitch between adjacent helices can increase along the length of the light absorbing portion. In this manner, an increasing or decreasing intensity gradient can be defined. Alternatively, a varied pitch can be defined by fluctuating the pitch or length between adjacent helices.

For purposes of illustration and not limitation, as embodied herein, the irradiating step preferably includes irradiating the light absorbing portion proximate to the contact area 326, 326' with light energy. For example, the light energy can be white light. The white light R can be provided by a halogen light source 328, but other light sources (incandescent, plasma and the like) are possible. For example, a halogen light source of 100 watts can be suitable. Light absorbing portion 330, 330' is provided proximate the contact area 326, 326'. As discussed, the light absorbing portion 330, 330' is preferably dark in color such that it absorbs white light energy creating heat sufficient to join the second tubular member 314 to the first tubular member 302 at the contact area 326, 326'. The light absorbing portion 330, 330' preferably includes a dark color gradient along its length. A greater amount of light energy is absorbed by the area of the light absorbing portion having a density of dark color relative to an area of the light absorbing portion having less density of dark color. In this manner, the fusion area defined by the absorption of light energy and the melting of the tubular members is configured to have an intensity gradient which corresponds to the light absorbing portion. Thus, the fusion area can be configured to include a stiffness gradient along the length thereof.

For the purpose of illustration and not limitation, as shown in FIG. 20, a first section 430 of the light absorbing portion having a greater width along its longitudinal axis absorbs a greater amount of energy than a second section 450 having a smaller width along the axis. Accordingly, the fusion area that corresponds to the first section of the light absorbing portion has a greater stiffness than the fusion area that corresponds to the second section of the light absorbing section.

Using ordinary white light, in contrast to intense laser light and the like provides numerous advantages. When other light sources of the prior art is used, expensive laser equipment is necessary to fuse plastic catheter segments. Moreover, it is necessary for an operator to use protective gear to prevent damage (such as to the eyes) when operating the equipment. In contrast, when using white light, such as from a halogen source, a much safer and less expensive result is obtained.

Light absorbing portion 330 can take on a variety of forms. For example, light absorbing portion 330 can be a separate component, or can be integrated with one or more of first tubular member 302 and second tubular member 314. Specifically, second tubular member 314 can be provided in the form of a black plastic material, such as polyimide.

First tubular member 302 can be provided accordingly in the form of a clear polyamide. As such, during the irradiation step, light will pass through first tubular member 302 and be absorbed by second tubular member 314 causing first tubular member 302 and/or second tubular member 314 to melt at the contact area 326, thereby permitting fusion. If second tubular member 314 is heated near its melting point during irradiation, the lumen of second tubular member can be supported by a mandrel 332 as depicted in FIG. 7. For example, a black second tubular member 314 composed of polyimide can have a melting temperature near 500 degrees centigrade, and a first polyamide nylon tubular member 302 can have a melting point near 100 degrees centigrade.

Figure 8A:
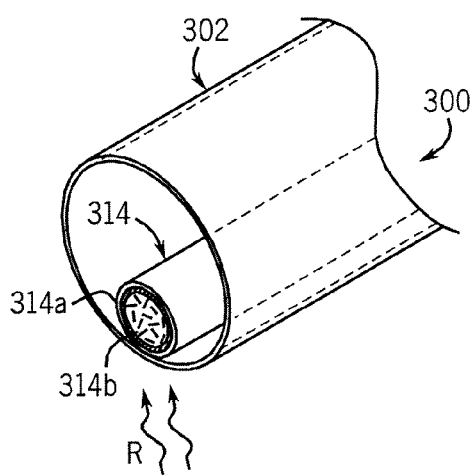
FIGS. 8(a)-8(c) are partial isometric views of a portion of a representative embodiment of a catheter made using a method in accordance with the present invention.
Figure 8B:
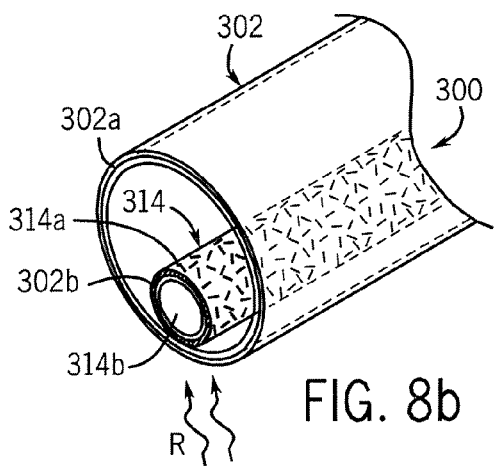
Figure 8C:
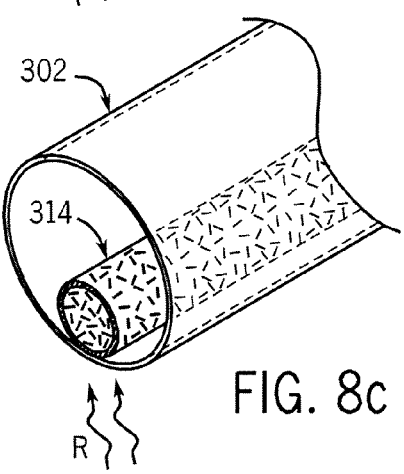

By way of further example, the black plastic material can be covered with a clear non-absorbing outer layer such as nylon by means of coextrusion, fusion etc. So that the inner black layer heats up and melts the outer layer without melting in itself, the outer layer can act like a hot-adhesive. For purposes of illustration and not limitation, as depicted in FIG. 8(*a*), inner layer 314*b* of second tubular member 314 is composed of such a black plastic material, and outer layer 314*a* is provided in the form of a plastic material that does not absorb significant light energy (e.g., transparent nylon). When catheter 300 is irradiated with white light R, inner layer 314*b* absorbs the radiation and increases in temperature, thereby partially melting outer layer 314*a*, resulting in outer layer 314*a* a being welded or fused to first tubular member 302.

Alternatively, as depicted in FIG. 8(*b*), inner layer 314*b* of second tubular member 314 is provided in the form of a plastic material that does not absorb significant light energy and outer layer 314*a* is provided in the form of black plastic material having a lower melting temperature than layer 314*b*. When catheter 300 is irradiated with white light R, outer layer 314*a* absorbs the radiation and increases in temperature, thereby partially melting inner layer 302*b* of first tubular member 302, resulting in outer layer 314*a* being welded to first tubular member 302.

As depicted in FIG. 8(*c*), second tubular member 314 is provided in the form of a dark plastic. As such, when irradiated with white light R, inner tube heats up. Depending on the melting temperature of first tubular member 302 and second tubular member 314, either or both tubular members 302, 314 can melt to create a bond.

Light absorbing portion 330 can also be applied, such as by printing or spray onto the surface of first tubular member 302 and/or second tubular member 314 in various geometric shapes and darkness to vary the degree of attachment between the first tubular member 302 and the second tubular member 314, as well as vary the degree of stiffness along the first and second tubular members. Moreover, light absorbing portion 330 can be incorporated into the body of first tubular member 302 and/or second tubular member 314 when formed, such as by during extrusion or dipping.

During the irradiation step, white light can be applied to the first tubular member 302 and second tubular member 304 by focusing the light down to a small area, such as an area half a centimeter in diameter. The light can be applied along the length of the catheter such that the light absorbing portion 330 or portions are all evenly heated permitting fusion along the length of the inner and outer members. While the focused radiation can be applied along a straight direction along the catheter 300, it may also be desirable to rotate the catheter while the focused radiation is translated along the length of the catheter, resulting in the radiation being applied along a "spiral" path. This provides the advantage of permitting the entire surface area of the catheter 300 to be heated. This can be useful, especially when the first tubular member 302 and second tubular member 314 are not aligned, such that the contact area 326 does not fall along a straight line. This method of applying radiation increases the contact area 326, and thus helps ensure the strength of the catheter 300.

In still further accordance with the invention, the method can also include the step of providing at least one mandrel having a light absorbing portion proximate to the contact area.

For purposes of illustration and not limitation, as embodied herein and as depicted in FIG. 9, a mandrel 332 is provided having a light absorbing portion 330 proximate to a contact area 326 defined where the first tubular member 302 adjoins the second tubular member 314.

The light absorbing portion 330 can include a linear segment along a length of the mandrel 332. The providing step can include positioning the mandrel 332 in the lumen 312, 324 of at least one of the first and second tubular members 302, 314, respectively with the light absorbing portion 330 proximate the contact area 326. The contact area 326 can be defined along at least a portion of the length of the first and second tubular members 302, 314. All or only a portion of the mandrel 332 can define a light absorbing portion 330. Light absorbing portion 330 can include any desired pattern (such as dots, squares, spirals and the like to permit different attachment patterns. In one preferred embodiment, as discussed above, light absorbing portion 330 includes a predetermined pattern having a gradient.

By way of further example, for purposes of illustration and not limitation, the providing step can include locating the mandrel 332 in the lumen 324 of the second tubular member 314 with the light absorbing portion 330 proximate the contact area 326. The light absorbing portion 330 can include a linear segment as depicted in FIG. 9. In accordance with yet a further aspect of the invention, the light absorbing portion 330 can include a plurality of segments.

In accordance with another aspect of the invention, the providing step can include locating the mandrel 334 outside the outer surface 308 of the first tubular member 302 with the light absorbing portion 330 proximate the contact area 326. The light absorbing portion can take any shape and can be provided in tubular or other forms. The arranging step can also include disposing at least a length of the first tubular member 302 adjacent a length of the second tubular member 314 with the outer surface 308 of the first tubular member 302 in contact with the outer surface 320 of the second tubular members 314.

One or more mandrels 332 can also be used to provide a crescent-shaped inflation channel. Advantageously, by using such a crescent-shaped mandrel, the alignment between the first and second tubular members 302, 314 can be optimized such that the contact area between the tubular members, and thus, the contact area, will lie along a straight line. Accordingly, white light can be applied along the catheter in a straight line without rotating the catheter during the irradiation step.

In further accordance with the invention, the method of the invention can further include the step of applying a pre-fixation device to at least one of the first and second tubular members to temporarily hold the first and second tubular members together prior to the irradiating step.

For purposes of illustration and not limitation, as embodied herein and as depicted in FIG. 10, the mandrel 334 acts as a pre-fixation device that is attached to at least one of the first and second tubular members 302, 314 to temporarily hold the first and second tubular members 302, 314 together prior and during the irradiating step. The pre-fixation device 334 can then be removed after the irradiating step, if desired.

In accordance with one embodiment of the invention, the pre-fixation device 334 includes heat shrink tubing. The heat shrink tubing can be removable, or if desired can remain affixed to the catheter. The shrink wrap tubing having a dark colored area to define a light absorbing portion 330.

By way of further example, the arranging step can further include disposing at least a length of the second tubular member 314 inside the lumen 312 of the first tubular member 302. The pre-fixation device 334 can include a removable insert disposed in the lumen 312 of the first tubular member 302, and be provided with a cross dimension sufficient to bias a portion of the outer surface 320 of the second tubular member 314 against a portion of the inner surface 310 of the first tubular member 302.

In accordance with another aspect of the invention, the mandrel can further define a pre-fixation device.

For purposes of illustration and not limitation, as embodied herein and as depicted in FIG. 10, the first and second tubular members 302, 314 are transparent to light energy. In accordance with this aspect of the invention, the mandrel 332 further defines a pre-fixation device 334. As depicted in FIG. 10, the mandrel 334 can have two or more portions 336, 338 that are configured to hold the first and second tubular members 302, 314 stationary relative to one another prior to the irradiation step.

In further accordance with the invention, the first tubular member and second tubular member can be arranged such that the second tubular member follows a helical path with respect to the first tubular member.

For purposes of illustration and not limitation, as embodied herein and as depicted in FIG. 11(a), second tubular member 314 follows a helical path inside of first tubular member 302. The bond is formed, for example, by providing either tubular member 302, 314 in the form of black plastic. During irradiation, the darker tube will heat up. Depending on the melting temperature of the material of each tube, one or both tubes will adhere itself to the other, resulting in a bond. Similarly, FIG. 11(b) depicts an arrangement having two side-by-side tubular members 314, 340 arranged inside of tubular member 302. One or more of tubular members 314, 340, or 302 can be provided in the form of black plastic. Irradiation will raise the temperature of tube 302 if provided in black plastic, facilitating fusion. Alternatively, tubular members 314 and/or 340 can be heated, resulting in a bond between all three tubular members 302, 314 and 340.

In further accordance with the method of the invention, it is also possible to fuse stiffening members to the inside of the catheter-shaft.

For purposes of illustration and not limitation, as embodied herein and as depicted in FIG. 12(a), polymeric stiffening member 342 having an outer surface 344 is provided inside of first tubular member 302. In accordance with this example, first tubular member does not absorb significant radiation, and stiffening member is provided in a form that does absorb significant radiation, such as a black plastic material. When stiffening member 342 is radiated with white light R, stiffening member 342 heats up and melts or fuses its outer surface 344 to first tubular member 302 or melts tubular member 302 to outer surface 344 cause fusion (or both) depending on the melting temperature of each material.

Alternatively, as depicted in FIG. 12(b), stiffening member 342 can be provided with a non-polymeric core 346, such as a metallic or carbon rod that is encased in black polymer. When this collection of components is irradiated, bonding can be accomplished as with the embodiment of FIG. 12(a).

In accordance with still another aspect of the invention, a method is provided further including the step of filtering the radiation used during the irradiation step.

For purposes of illustration and not limitation, as embodied herein and as depicted in FIG. 13, filter 348 is interposed between radiation source 328 and catheter 300. As such, selected wavelengths can be chosen to irradiate catheter 300 to cause fusion. Filters for the white light can be used to allow only a more narrow band of light frequencies to pass. The band of frequencies can be adapted to the spectra of the materials that are intended to absorb light energy and/or melt. Also, special light sources can be chosen based on the light frequencies that are emitted in order to accommodate the materials which are intended to be melted, and those that are not intended to be melted. In addition to purely white light and subsections of that spectrum, infrared and ultraviolet wavelengths can also be used if desired. Moreover, light sources of certain frequencies can be combined with filters in order to make the absorbance/non-absorbance more specific for certain combinations of materials.

In accordance with another aspect of the invention, a mask can be used to create patterns on the components of the catheter.

For purposes of illustration and not limitation, as embodied herein and as depicted in FIG. 14, a mask 350 is provided having a preselected pattern to permit radiation to be exposed to only certain portions of the catheter 300.

In accordance with another aspect of the invention, one or more light conductive elements can be used to provide radiation during the radiation step.

For purposes of illustration and not limitation, as embodied herein and as depicted in FIGS. 15(a)-15(c), light conductive element 352 is provided. Light conductive element 352 radiates white light along its length to heat one or both of first and second tubular members 302, 314, as desired to promote fusion. Light conductive element 352 can be directed through either lumen 324 of second tubular member 314, lumen 312 of outer tubular member 302, or both. Moreover, any beam of white light or radiation R can be directed over the catheter 300 through light conductive element 352, as desired to accomplish fusion.

By way of further example, it is possible to include multiple tubular members inside of an outer tubular member. For example, as depicted in FIG. 16(a), three tubular members 314, 340, 354 can be provided inside of tubular member 302. Tubular members 314, 340, 354 can be provided with different cross sectional shapes and thicknesses as depicted in FIG. 16(b). Moreover, as depicted in FIG. 16(c), each of tubular members 314, 340 and 354 can be provided in the form of multilayer tubes 314a, 314b, 340a, 340b, 354a, 354b, each tube having layers made of different materials.

In further accordance with the invention, radiation can be used to melt adhesive material to affix portions of a catheter to one another in a similar manner as described above.

Figure 17A:
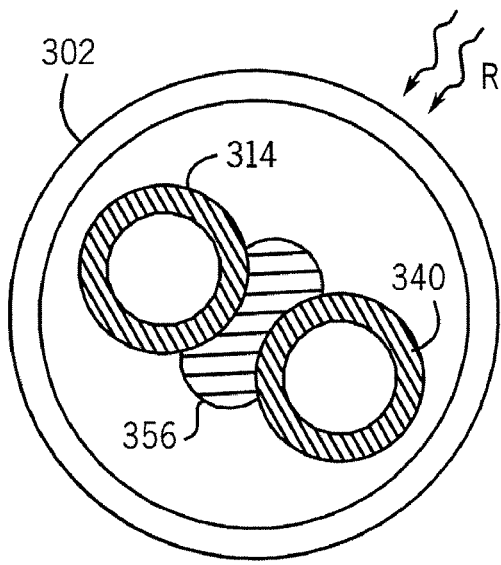
FIGS. 17(a)-17(b) are end views of a portion of alternative embodiments of catheters made in accordance with the present invention.
Figure 17B:
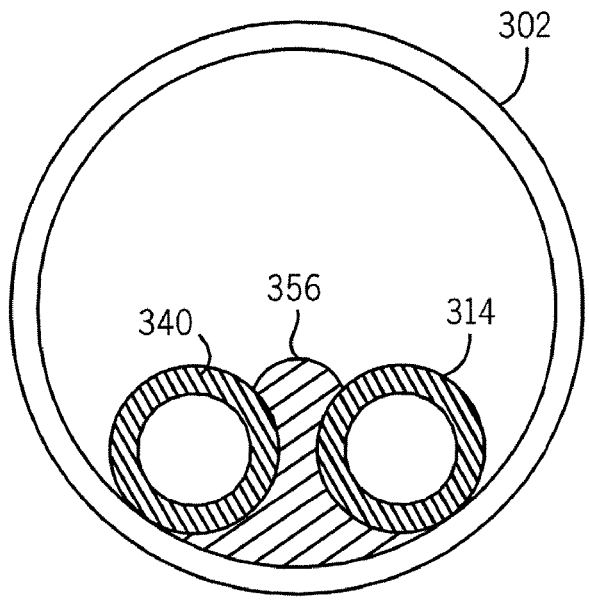

For purposes of illustration and not limitation, as depicted in FIG. 17, it is possible to provide connecting material 356 that can be melted by radiation, acting as an adhesive to affix tubular members 302, 314 and 340 to one another. Connecting material can connect interior tubular members 314 and 340 to one another, as depicted in FIG. 17(a), or to one another and tubular member 302, as depicted in FIG. 17(b).

Figure 18:
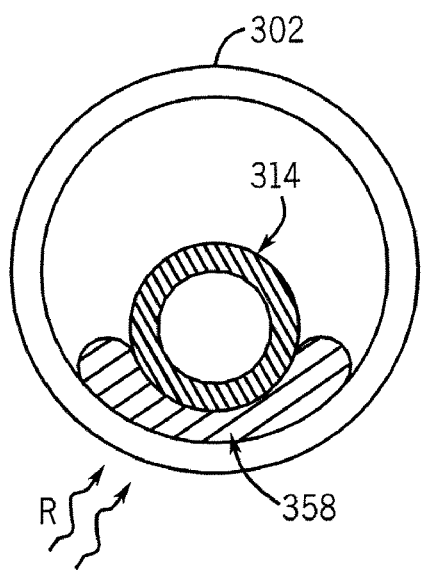
FIG. 18 is an end view of a portion of a catheter made in accordance with the present invention.

Moreover, as depicted in FIG. 18, a crescent shaped member 358 can be provided made of a meltable material, such as black plastic. If crescent shaped member 358 is selected to have a lower melting temperature than tubular members 302, 314, crescent shaped member can melt upon exposure to radiation to fuse tubular members 302, 314 to one another.

Many different types of catheters and portions thereof can be constructed using support members (e.g., 126, FIG. 3) and using the methods of construction described herein. For example, the catheters described in U.S. Patent Application Ser. No. 60/575,643, U.S. Patent Application Ser. No. 60/654,022, U.S. Non-Provisional Patent Application filed on even date herewith identified by Winston & Strawn Ser. No. 60/575,643 titled "Catheter Having Main Body Portion With Coil-Defined Guidewire Passage" and U.S. Non-Provisional Patent Application filed on even date herewith identified by Winston & Strawn Ser. No. 60/654,022 titled "Catheter Having First And Second Guidewire Tubes And Overlapping Stiffening Members" can be constructed in accordance with these techniques. These patent applications are hereby incorporated by reference herein in their entirety.

The methods and systems of the present invention, as described above and shown in the drawings, provide for a catheter with superior properties including superior flexibility and pushability. It will be apparent to those skilled in the art that various modifications and variations can be made in the device and method of the present invention without departing from the spirit or scope of the invention. Thus, it is intended that the present invention include modifications and variations that are within the scope of the appended claims and their equivalents.

What is claimed is:

1. A catheter comprising:
   an outer tubular member having a length, an outer surface, an inner surface and a lumen therein;
   an inner tubular member having an outer surface, an inner surface and a lumen therein, at least a length of the inner lumen is disposed in the lumen of the outer tubular member; and
   a support member disposed in the lumen of the outer tubular member adjacent the inner tubular member, the support member biasing a portion of the outer surface of the inner tubular member against a portion of the inner surface of the outer tubular member;
   wherein at least one of the inner tubular member and the support member is not attached to the outer tubular member.

2. The catheter of claim 1, wherein the support member is not attached to at least one of the inner tubular member and the outer tubular member.

3. The catheter of claim 1, wherein the support member is not attached to either the inner tubular member or the outer tubular member.

4. The catheter of claim 1, wherein the support member is a tubular structure having a length and a lumen therein.

5. The catheter of claim 4, wherein the tubular structure is at least partially compressed to bias the inner tubular member against the outer tubular member.

6. The catheter of claim 1, wherein the support member extends longitudinally along at least a portion of the length of the inner tubular member disposed within the outer tubular member.

7. The tubular member of claim 1, wherein the support member extends along the entire length of the inner tubular member disposed within the outer tubular member.

8. The catheter of claim 1, wherein a plurality of support members are disposed along the length between the outer surface of the inner tubular member and the inner surface of the outer tubular member.

9. The catheter of claim 8, wherein the plurality of support members are interconnected.

10. The catheter of claim 8, wherein each support member has a length, the lengths of the support members being varied.

11. The catheter of claim 1, wherein the lumen of the inner tubular member defines a guidewire lumen.

12. The catheter of claim 1, wherein the lumen of the outer tubular member defines an inflation lumen.

13. The catheter of claim 11, wherein the support member has a lumen defined therein for passage of inflation fluid.

14. The catheter of claim 1, wherein the support member is a tubular member having a length and a lumen, the tubular member formed from a metallic material.

15. The catheter of claim 14, wherein the tubular member includes a plurality of cuts spirally disposed about the tubular member and along a length thereof.

16. The catheter of claim 14, wherein the plurality of cuts transition from a first pitch to a second pitch along the length of the tubular member, the first pitch and the second pitch being different.

17. A catheter comprising:
   an elongate main body including at least a proximal shaft section and a distal shaft section, and a lumen therein;

a guidewire tube disposed along a length of the lumen of the elongate main body, and having a proximal guidewire port, a distal guidewire port, and a guidewire lumen therebetween;

a support member disposed in the lumen of the elongate main body adjacent the guidewire tube, the support member biasing a portion of an outer surface of the guidewire tube against a portion of an inner surface of the elongate main body;

wherein the support member applies a continuous biasing force against the outer surface of the guidewire tube.

18. The catheter of claim 17, wherein the support member is a tubular structure having a length and a lumen therein.

19. The catheter of claim 18, wherein the tubular structure is at least partially compressed to bias the guidewire tube against the elongate main body.

20. The catheter of claim 17, wherein the support member extends longitudinally along at least a portion of the length of the guidewire tube disposed within the elongate main body.

21. The catheter of claim 17, wherein the lumen of the elongate main body defines an inflation lumen.

22. The catheter of claim 21, wherein the support member has a lumen defined therein for passage of inflation fluid.

23. The catheter of claim 21, wherein at least one of the elongate main body and guidewire tube is a tubular member including a plurality of cuts spirally disposed about the tubular member, the plurality of cuts defining a pitch between adjacent cuts.

24. The catheter of claim 23, wherein the a plurality of cuts is configured to define a varied flexibility or stiffness along the length of the at least one elongate main body or the guidewire tube.

25. The catheter of claim 24, wherein the plurality of spiral cuts transition from a first pitch to a second pitch, the first pitch being greater than the second pitch.

26. The catheter of claim 23, wherein the tubular member is a metallic member.

27. The catheter of claim 23, wherein the tubular member includes a polymeric coating applied to an outer surface of the tubular member.

* * * * *